United States Patent
Furling et al.

(10) Patent No.: US 10,799,556 B2
(45) Date of Patent: Oct. 13, 2020

(54) TREATMENT OF MYOTONIC DYSTROPHY

(71) Applicants: ASSOCIATION INSTITUT DE MYOLOGIE, Paris (FR); CENTRE NATIONAL DE LA RECHERCHE SCIENTIFIQUE, Paris (FR); INSTITUT NATIONAL DE LA SANTE ET DE LA RECHERCHE MEDICALE, Paris (FR); UNIVERSITE PIERRE ET MARIE CURIE (PARIS 6), Paris (FR)

(72) Inventors: Denis Furling, Joinville-le-Pont (FR); Nicolas Sergeant, Ronchin (FR); Marie-Laure Caillet-Boudin, Tournai (BE); Ludovic Arandel, Saint Maur des Fosses (FR)

(73) Assignees: ASSOCIATION INSTITUT DE MYOLOGIE, Paris (FR); CENTRE NATIONAL DE LA RECHERCHE SCIENTIFIQUE, Paris (FR); INSTITUT NATIONAL DE LA SANTE ET DE LA RECHERCHE MEDICALE, Paris (FR); UNIVERSITÉPIERRE ET MARIE CURIE (PARIS 6)

( * ) Notice: Subject to any disclaimer, the term of this patent is extended or adjusted under 35 U.S.C. 154(b) by 0 days.

(21) Appl. No.: 15/303,769

(22) PCT Filed: Apr. 14, 2015

(86) PCT No.: PCT/EP2015/058111
§ 371 (c)(1),
(2) Date: Oct. 13, 2016

(87) PCT Pub. No.: WO2015/158740
PCT Pub. Date: Oct. 22, 2015

(65) Prior Publication Data
US 2017/0035841 A1    Feb. 9, 2017

(30) Foreign Application Priority Data

Apr. 14, 2014    (WO) .................. PCT/EP2014/057553

(51) Int. Cl.
*A61K 38/17*    (2006.01)
*A61K 48/00*    (2006.01)

(52) U.S. Cl.
CPC ........ *A61K 38/1709* (2013.01); *A61K 48/005* (2013.01); *A61K 48/0075* (2013.01)

(58) Field of Classification Search
None
See application file for complete search history.

(56) References Cited

U.S. PATENT DOCUMENTS

2010/0130594 A1*    5/2010    Barkats .............. A61K 48/0075
514/44 R

FOREIGN PATENT DOCUMENTS

WO    WO 2010/044894    4/2010

OTHER PUBLICATIONS

Chamberlain, C. M. et al. "Mouse model of muscleblind-like 1 overexpression: skeletal muscle effects and therapeutic promise" *Human Molecular Genetics*, Nov. 1, 2012, pp. 4645-4654, vol. 21, No. 21.
Foff, E. P. et al. "Therapeutics Development in Myotonic Dystrophy Type 1" *Muscle & Nerve*, Aug. 23, 2011, pp. 160-169, vol. 44, No. 2.
Tran, H. et al. "Analysis of Exonic Regions Involved in Nuclear Localization, Splicing Activity, and Dimerization of Muscleblind-like-1 Isoforms" *The Journal of Biological Chemistry*, May 6, 2011, pp. 16435-16446, vol. 286, No. 18.
Written Opinion in International Application No. PCT/EP2015/058111, dated Aug. 7, 2015, pp. 1-6.

* cited by examiner

*Primary Examiner* — Michael D Burkhart
(74) *Attorney, Agent, or Firm* — Saliwanchik, Lloyd & Eisenschenk

(57) ABSTRACT

The present invention relates to compositions and methods for treating myotonic dystrophy.

Figure 1:
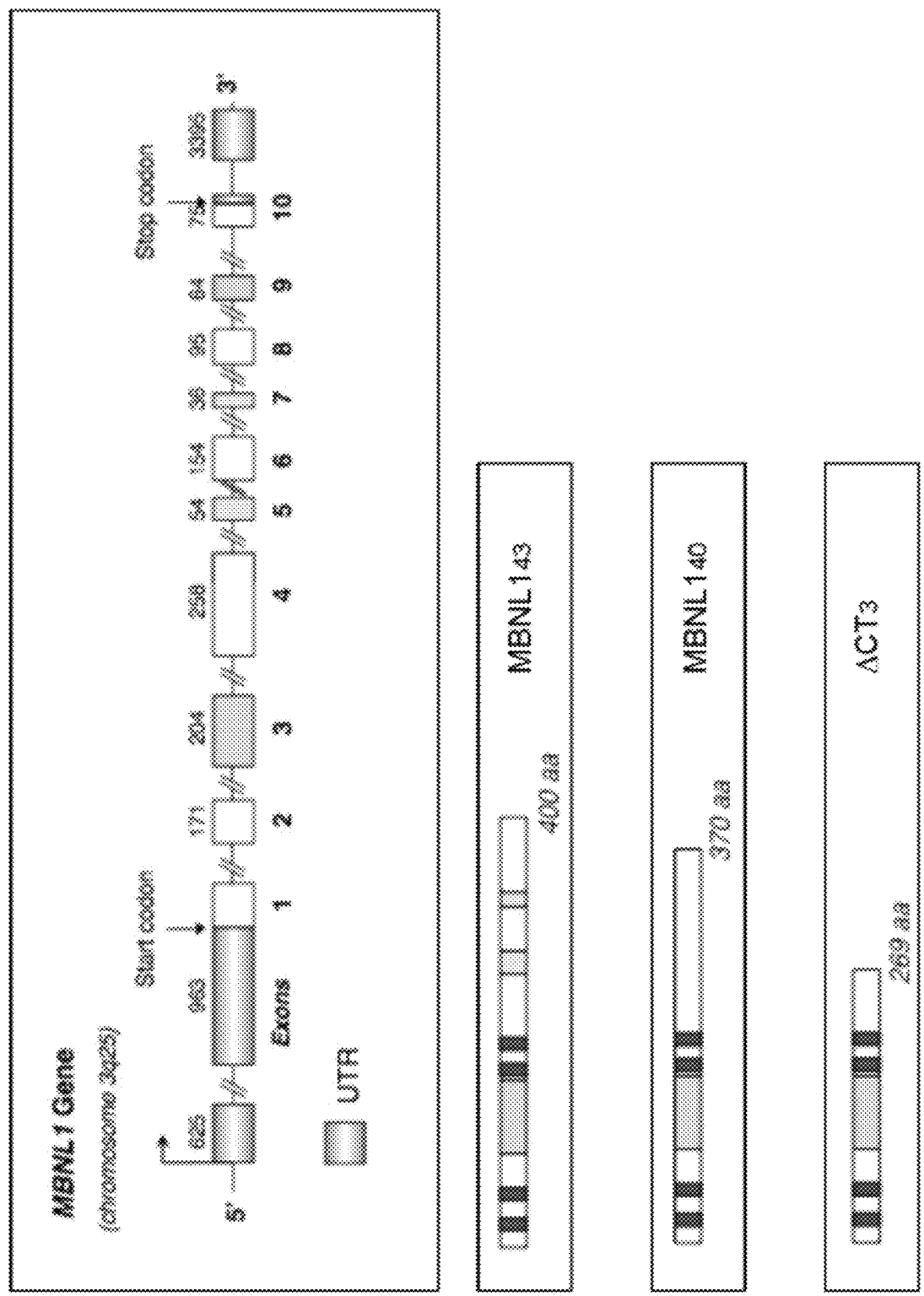

10 Claims, 19 Drawing Sheets
(10 of 19 Drawing Sheet(s) Filed in Color)
Specification includes a Sequence Listing.

TREATMENT OF MYOTONIC DYSTROPHY

FIELD OF THE INVENTION

The present invention relates to compositions and methods for treating myotonic dystrophy.

BACKGROUND OF THE INVENTION

Myotonic dystrophy type 1 (DM1), one of the most common neuromuscular disorders in adult, is an inherited autosomal dominant disease caused by an unstable CTG expansion located in the 3' untranslated region (UTR) of the dystrophia myotonica protein kinase (DMPK) gene (Brook et al. 1992). The number of CTG varies from fifty to more than several thousand of repeats in affected patients whereas unaffected individuals have less than 38 repeats, and globally there is a correlation between the size of the CTG repeats, the severity of the disease and inversely with the age of onset (Hunter et al. 1992; Tsilfidis et al. 1992). Clinical features of DM1 are variable but commonly include myotonia, progressive muscle weakness and atrophy as well as cardiac conduction defects but also extra-muscular symptoms such as cognitive dysfunctions, cataract, hypogonadism and endocrine deficiencies (Harper 2001).

The pathogenic CTG tract is transcribed and gives rise to RNAs containing expanded CUG repeats (CUGexp-RNAs) located in the 3' UTR of the DMPK transcripts, which are responsible for a toxic RNA gain-of-function mechanism in DM1 pathogenesis (Klein et al. 2011). CUGexp-RNAs that are retained in nuclei as discrete aggregates or foci alter the function of RNA splicing factors members of the MBNL and CELF families resulting in alternative splicing misregulation of a specific group of transcripts in affected DM1 tissues (Taneja et al. 1995; Ranum and Cooper 2006). Abnormal regulation of splicing events leads mainly to the re-expression of a fetal splicing pattern in DM1 adult tissues, and missplicing events affecting the CLC-1, INSR and BIN1 pre-mRNAs have been associated respectively with myotonia, insulin resistance and muscle weakness (Savkur et al. 2001; Charlet et al. 2002; Mankodi et al. 2002; Fugier et al. 2011). A recent study performed on a cohort of fifty DM1 patients confirmed forty-two splicing defects in affected skeletal muscles, and showed that these splicing changes were specific to DM1 when compared to other muscle disorders, and mainly attributable to MBNL1 loss-of-function (Nakamori et al. 2013).

MBNL1 is a member of the muscleblind-like RNA-binding protein family including MBNL1, -2 and -3 (Pascual et al. 2006), and is the major MBNL protein expressed in adult skeletal muscle (Kanadia et al. 2003; Holt et al. 2009). MBNL1 like the other MBNL protein paralogues binds to expanded CUG repeats with high affinity, and colocalizes with nuclear foci of CUGexp-RNA in DM1 muscle cells (Miller et al. 2000; Fardaei et al. 2001). Sequestration of MBNL1 in these ribonucleoprotein complexes due to the large number of CUG repeats in mutant RNAs leads to its loss-of-function, and consequently to alternative splicing misregulation of several target pre-mRNAs, including MBNL1 itself. Consistent with this hypothesis, Mbnl1 knockout mice reproduces most of the deregulated splicing events observed in muscle samples of DM1 patients or DM1 mouse model expressing CUGexp-RNAs (Mankodi et al. 2000; Kanadia et al. 2003; Lin et al. 2006; Du et al. 2010). Moreover overexpression of functional and full length MBNL1 (isoform 40 or 41) in the skeletal muscles of DM1 mice is sufficient to correct splicing defects and abolish myotonia, hallmarks of DM1 disease (Kanadia et al. 2006; Chamberlain and Ranum 2012). Furthermore, in WO2010/044894 it is proposed to administer a MBNL protein or a functional variant thereof, i.e. a variant that retains de biological activity of a MBNL protein, in the form of a chimeric polypeptide conjugated with a targeting moiety. This document does not disclose the use of a non-functional MBNL polypeptide for the treatment of DM1. In addition, disruption of MBNL2, which is prominently expressed in the brain, deregulates specific splicing events in mice that are similarly misregulated in human DM1 brains supporting a prominent role of MBNL2 loss-of-function in the pathological changes in the human disease (Charizanis et al. 2012). Taken together, these results support MBNL loss-of-function as a key mechanism involved in RNA toxicity induced by expanded CUG repeats in DM1.

Modified oligonucleotide antisens approaches that interfere with CUGexp-RNAs to release MBNL1 from the foci have already been proposed for reversing splicing misregulations and myotonia in a DM1 mouse model. However, alternate and efficient means for reversing splicing misregulations and counteracting clinical symptoms such as myotonia in myotonic dystrophy are still needed.

SUMMARY OF THE INVENTION

The purpose of the present invention is to provide new tools and methods for myotonic dystrophy treatment. The present invention is based on the evidence provided herein that a modified MBNL polypeptide ectopically expressed, in particular through the use of viral vectors, is effective to counteract CUGexp-RNA toxicity both in vitro and in vivo.

An aspect of this invention relates to a modified MBNL polypeptide. As provided below, the modified MBNL polypeptide of the invention has a reduced splicing activity, in particular a splicing activity reduced by at least 50%, in particular by at least 60%, 70%, 75%, 80%, 85% or by at least 90% or even by at least 95%, when compared to splicing activity of full-length MBNL protein but maintains its YGCY binding property. In particular, the modified MBNL polypeptide of the invention is able to bind pathological CUG repeat. Moreover, the modified MBNL polypeptide used herein can counteract the CUGexp-RNA toxicity by releasing sequestered endogenous MBNL such as MBNL1 and MBNL2 from the CUGexp-RNA aggregates in order to restore the function of these endogenous MBNL proteins.

The modified MBNL polypeptide of the present invention is used in the treatment of myotonic dystrophies. Another aspect relates to a method for treating myotonic dystrophies, comprising administering to a subject in need thereof an effective amount of a modified MBNL polypeptide according to the invention. A further aspect of the invention is the use of a modified MBNL polypeptide as described herein, for the manufacture of a medicament for use in the treatment of myotonic dystrophies.

Another aspect disclosed herein is the use of the modified MBNL polypeptide according to the invention for displacing an endogenous MBNL protein, such as endogenous MBNL1 or MBNL2, from CUG repeats in a cell or organism in need thereof, and thereby reversing deregulated splicing events induced by the CUGexp-RNA expression. In a particular embodiment, the modified MBNL polypeptide is provided to the cell or organism using a viral vector.

LEGEND OF THE FIGURES

The patent or application file contains at least one drawing executed in color. Copies of this patent or patent application publication, with color drawing(s), will be provided by the Office upon request and payment of the necessary fee.

FIG. 1: Genomic DNA organization of human MBNL1 gene. Order and names of exons are shown as well as the length in nucleotides of each exon. Clear gray boxes represent UTR. Color boxes represent cassette exons. Empty boxes represent constitutive exons. Alternative splicing of MBNL1 alternative cassettes leads to more than ten isoforms including $MBNL1_{43}$ or $MBNL1_{40}$. The length in amino acids (aa) is indicated and the Dark gray boxes represent $C_3H_1$ zinc finger motifs. Two are located in MBNL1 exon 2 and the two others are located in MBNL1 exon 4. The modified MBNL1 polypeptide (herein referred as ΔCT3) is the truncated MBNL1 construct lacking the C-terminal domain following the fourth $C_3H_1$ zinc finger motif.

Figure 2:
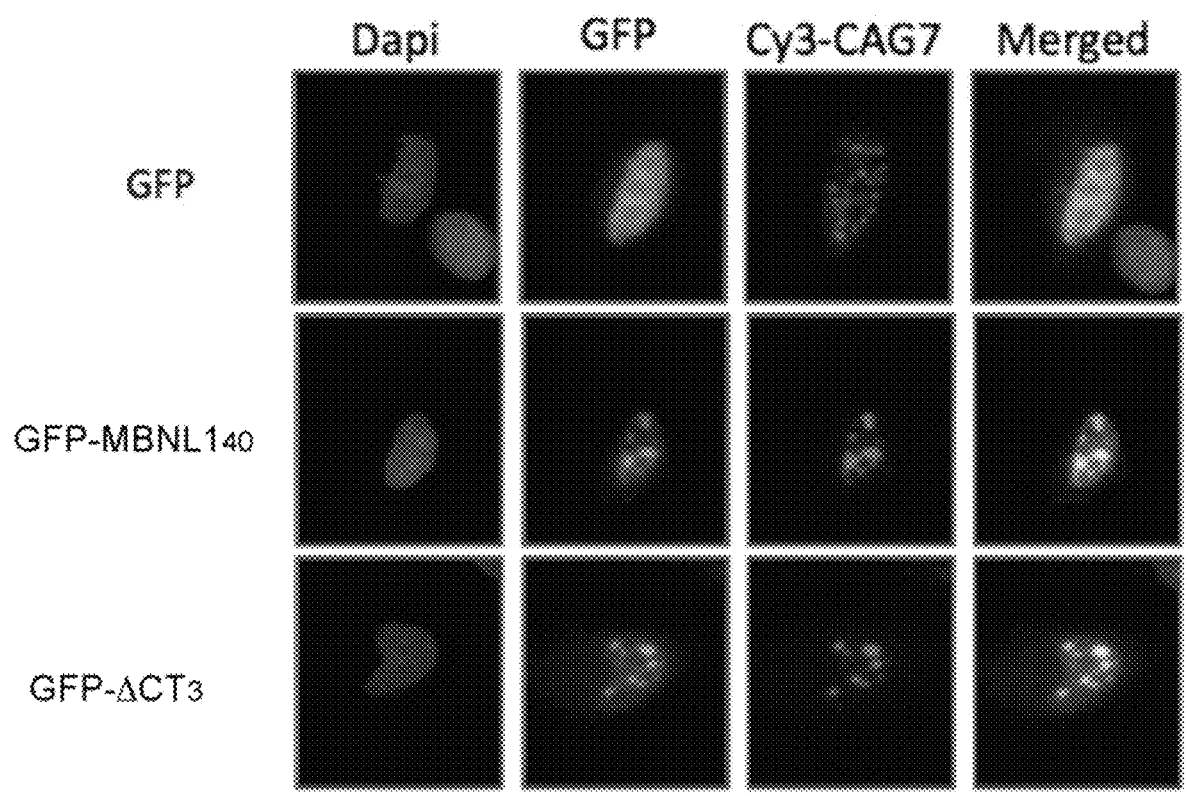

FIG. 2: ΔCT3 colocalizes with nuclear CUGexp-RNA aggregates in vitro. GFP, GFP-ΔCT3 or GFP-$MBNL1_{40}$ constructs were co-transfected with 960CTG repeats in Hela cells. CUGexp-RNA foci were visualized by FISH using a Cy3-CAG7 probe.

Figure 3:
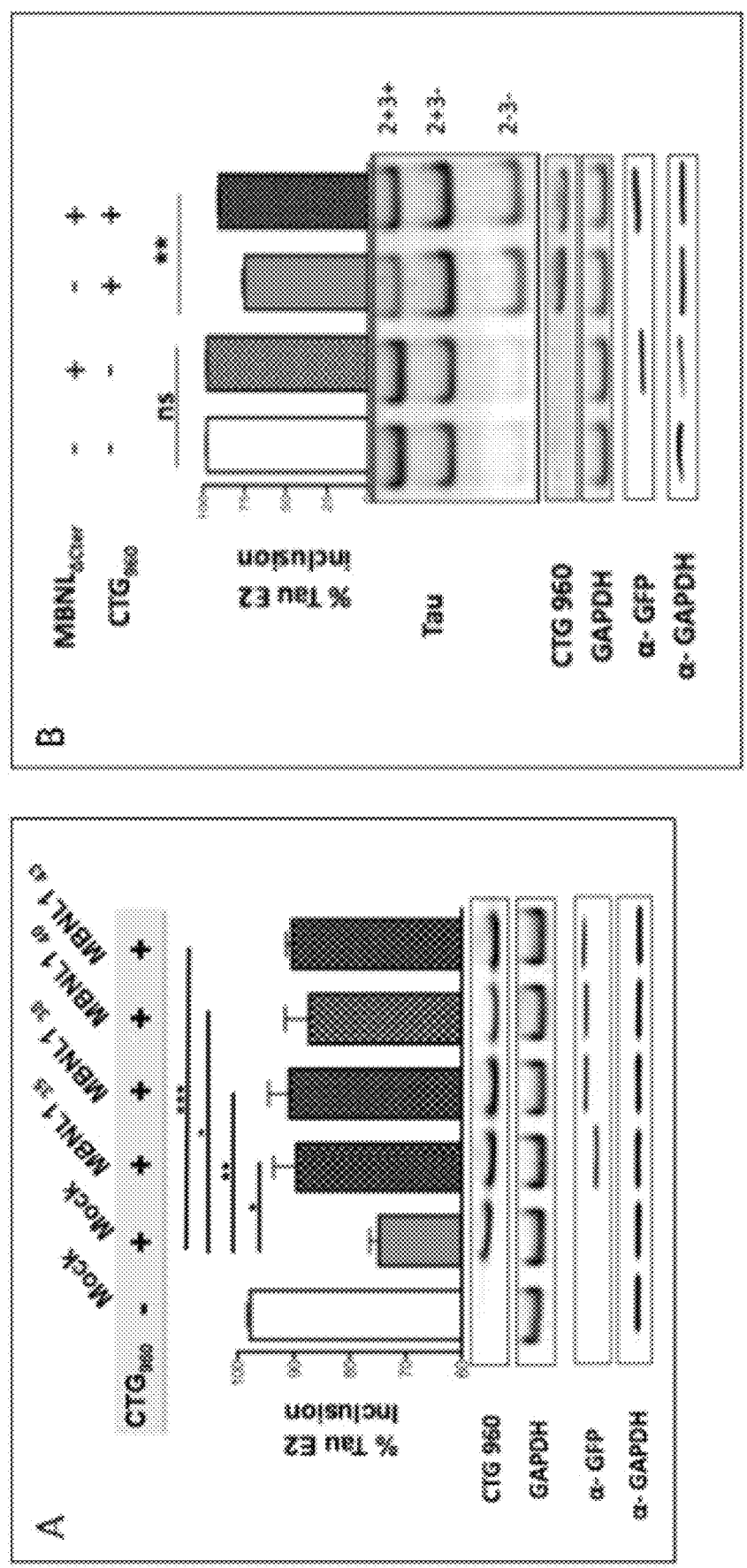

FIG. 3: Expression of various MBNL1 isoforms as well as ΔCT3 construct restores DM1 deregulated splicing of Tau exon 2/3 minigene. The Tau exon 2/3 minigene comprises the two alternate cassettes 2 and 3 insert in the psvIRB splicing reporter minigene (Tran et al. 2011). $MBNL1_{35}$ or $_{38}$ or $_{41}$ or $_{43}$ isoforms (panel A) or GFP-ΔCT3 panel B) were co-expressed with Tau exon 2/3 minigene and a plasmid containing 960 interrupted CTG repeats in Hela cells, as previously described (Tran et al. 2011). The percentage of inclusion of Tau E2 was calculated and established following RT-PCR using primers surrounding Tau exon 2 and exon 3.

Figure 4:
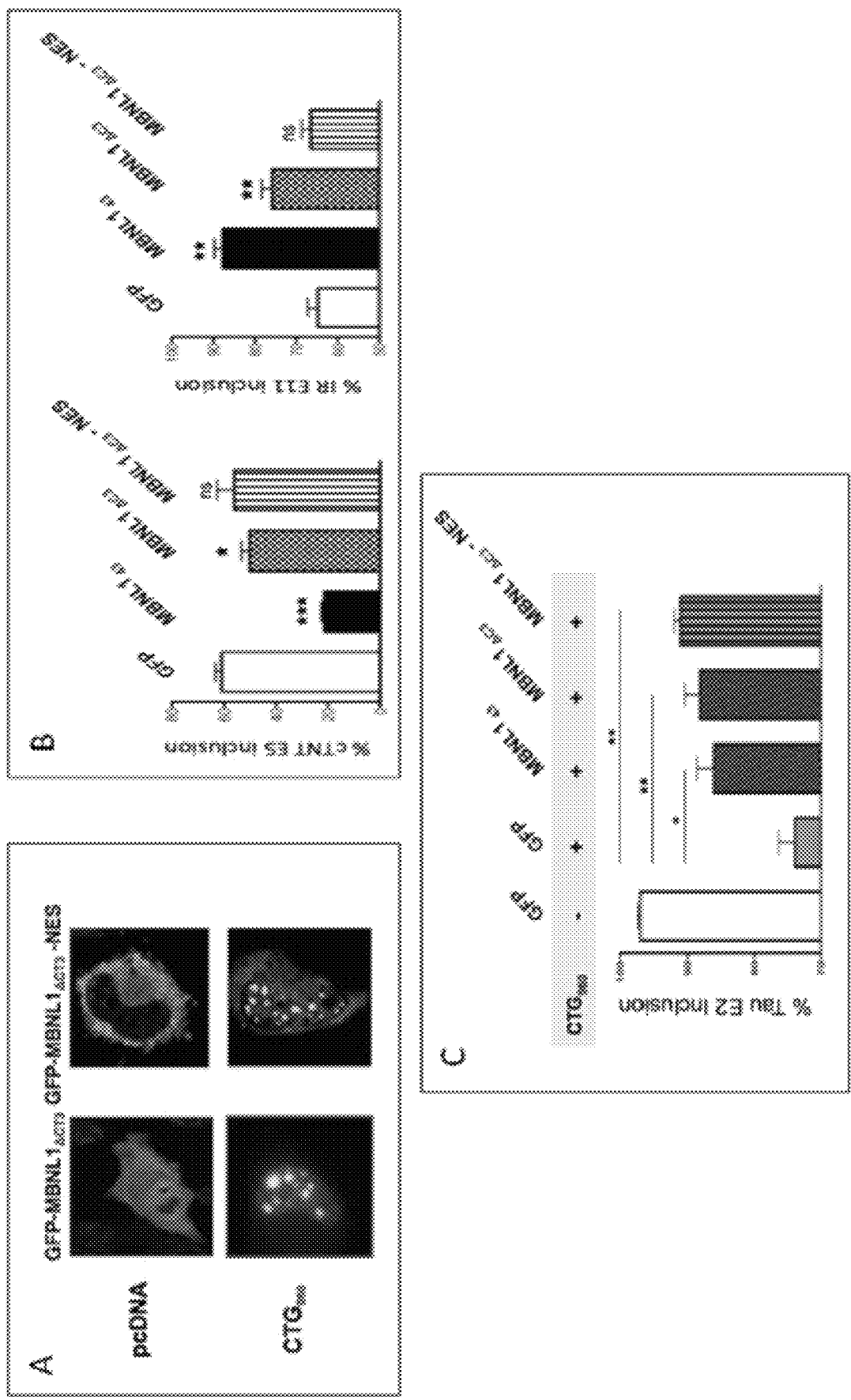

FIG. 4: Nuclear localization of ΔCT3 is required to modulate splicing events. A) GFP-ΔCT3 constructs containing or not a nuclear export signal (NES) were co-expressed or not with 960 CTG repeats in Hela cells. B) Inclusion of cTNT exon 5 or IR exon 11 was assessed by RT-PCR after co-tranfection of MBNL or GFP constructs and cTNT exon 5 or IR exon 11 minigenes in Hela cells. C). Inclusion of Tau exon 2 was analyzed in Hela cells co-transfected with Tau exon 2/3 minigene, 960 CTG repeats and MBNL or GFP constructs.

Figure 5:
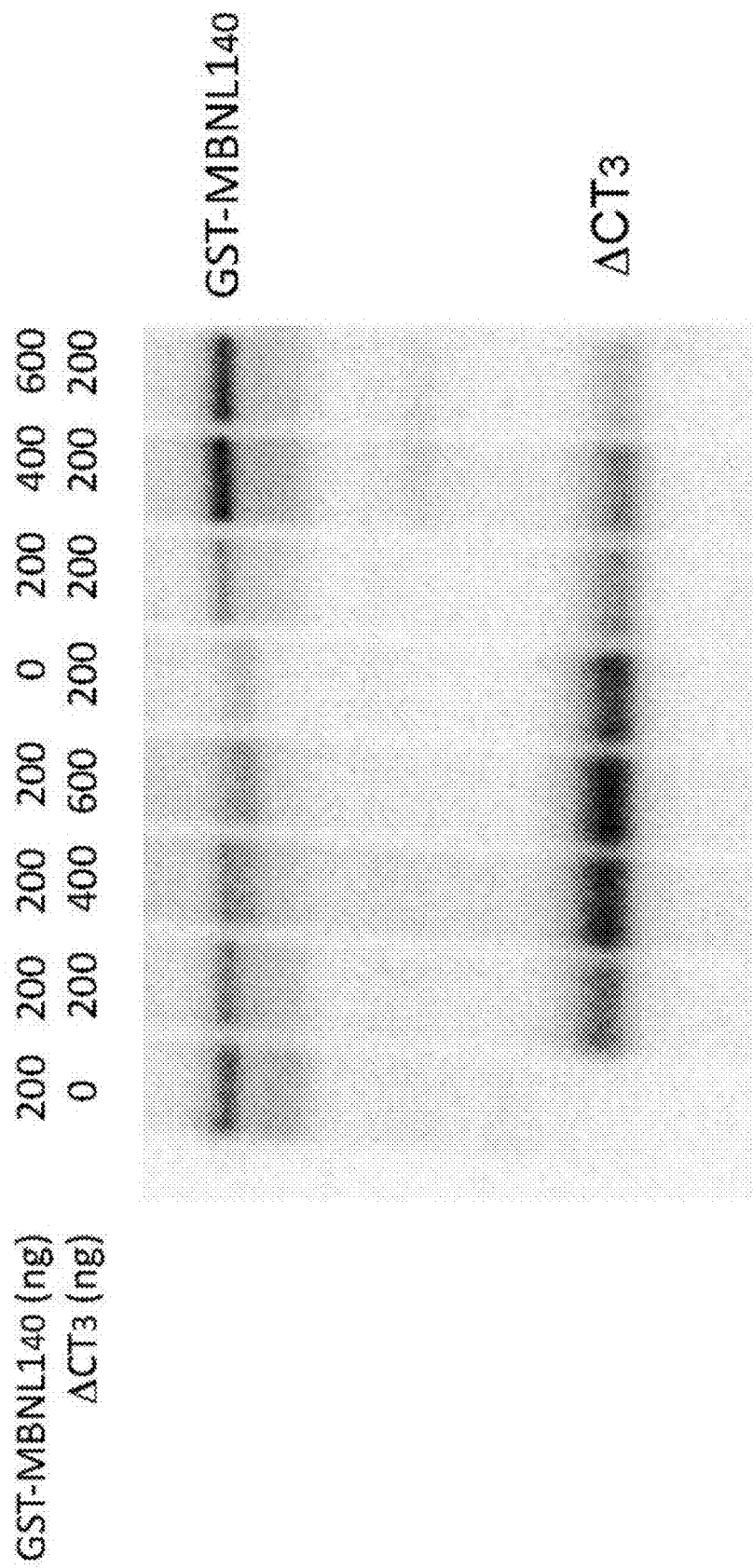

FIG. 5: ΔCT3 is able to displace MBNL1 from CUG repeats in vitro. Recombinant $MBNL1_{40}$ (or ΔCT3) protein was cross-linked to in vitro transcribed $^{32}P$ RNA containing 95 CUG repeats in the absence or presence of incremental concentrations of recombinant ΔCT3 ($MBNL1_{40}$) protein.

Figure 6:
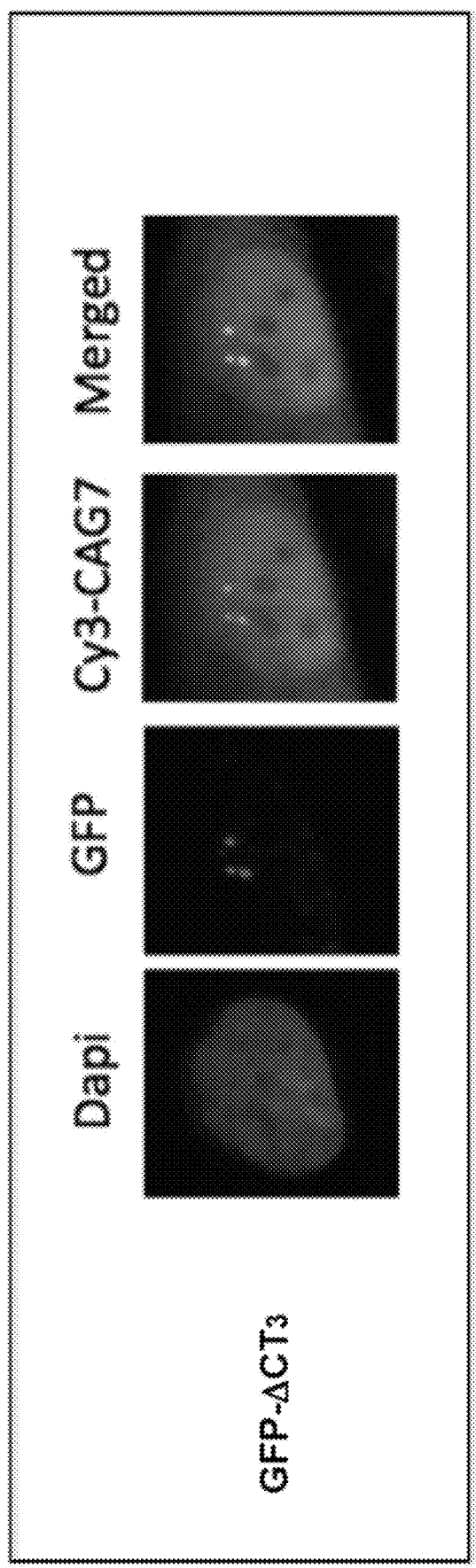

FIG. 6: ΔCT3 colocalizes with nuclear CUGexp-RNA in human DM1 muscle cells. Primary DM1 muscle cells were transduced with lentiviral vectors containing the cDNA encoding the GFP-ΔCT3. CUGexp-RNA foci were visualized by FISH using a Cy3-CAG$_7$ probe.

Figure 7A:
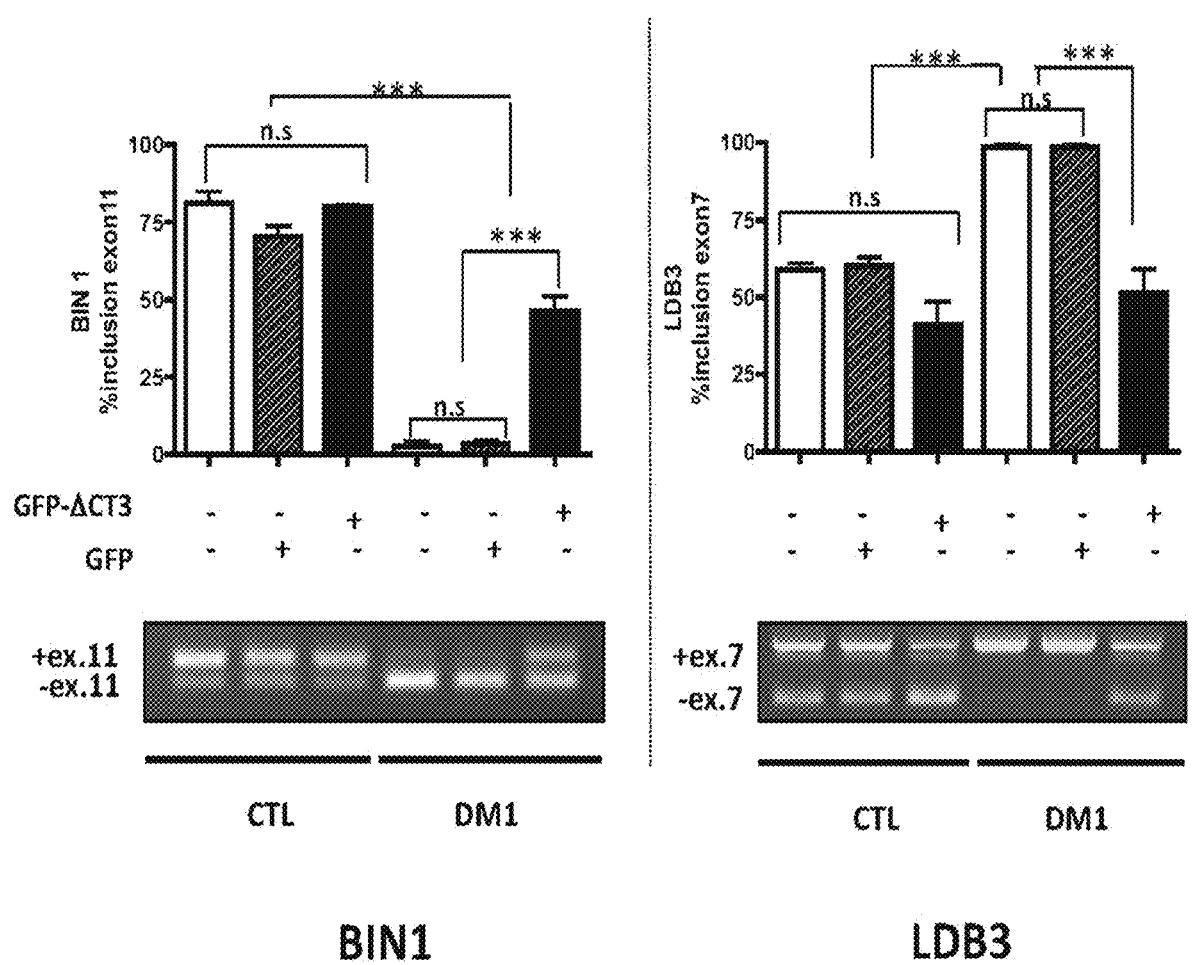
Figure 7A:
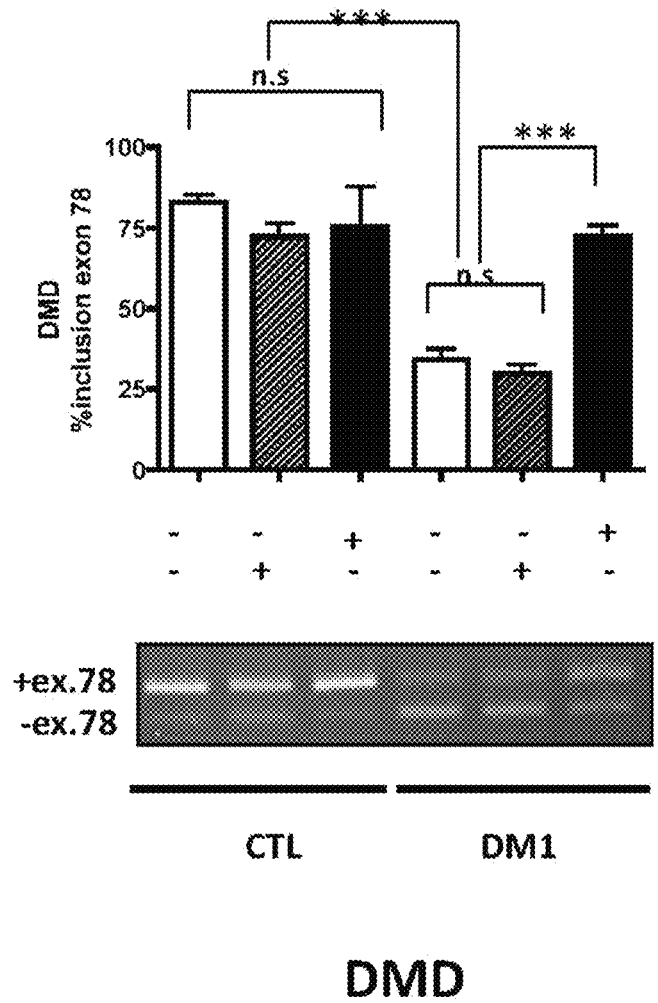

FIG. 7A: ΔCT3 normalizes missplicing events in differentiated human DM1 muscle cells. Primary human DM1 and non-DM1 muscle cells were transduced or not with lentiviral vectors expressing GFP-ΔCT3 or GFP alone. Splicing profile of BIN1 exon 11, LDB3 exon 7 and DMD exon 78 transcripts were analyzed by RT-PCR.

Figure 7B:
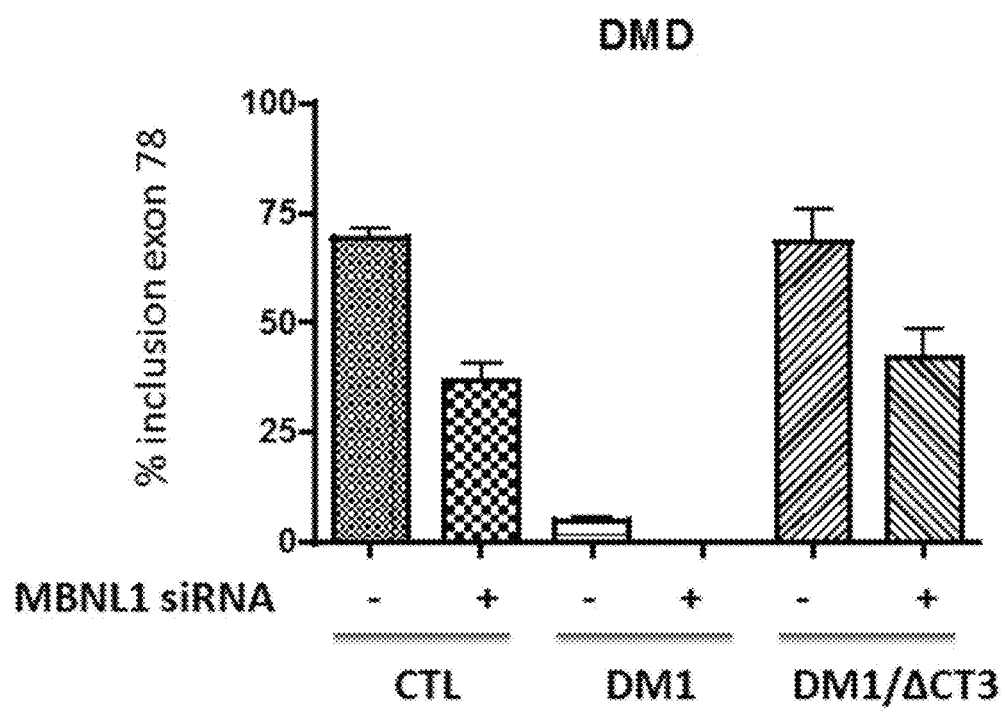

FIG. 7B: Differentiated muscle cells (Control, DM1 or DM1 expressing C) were transfected or not with MBNL1 siRNA directed again the C-terminus exon 9 (present in MBNL1 but not in ΔCT3 sequences). Splicing profile of DMD exon 78 transcripts was analyzed by RT-PCR.

Figure 8:
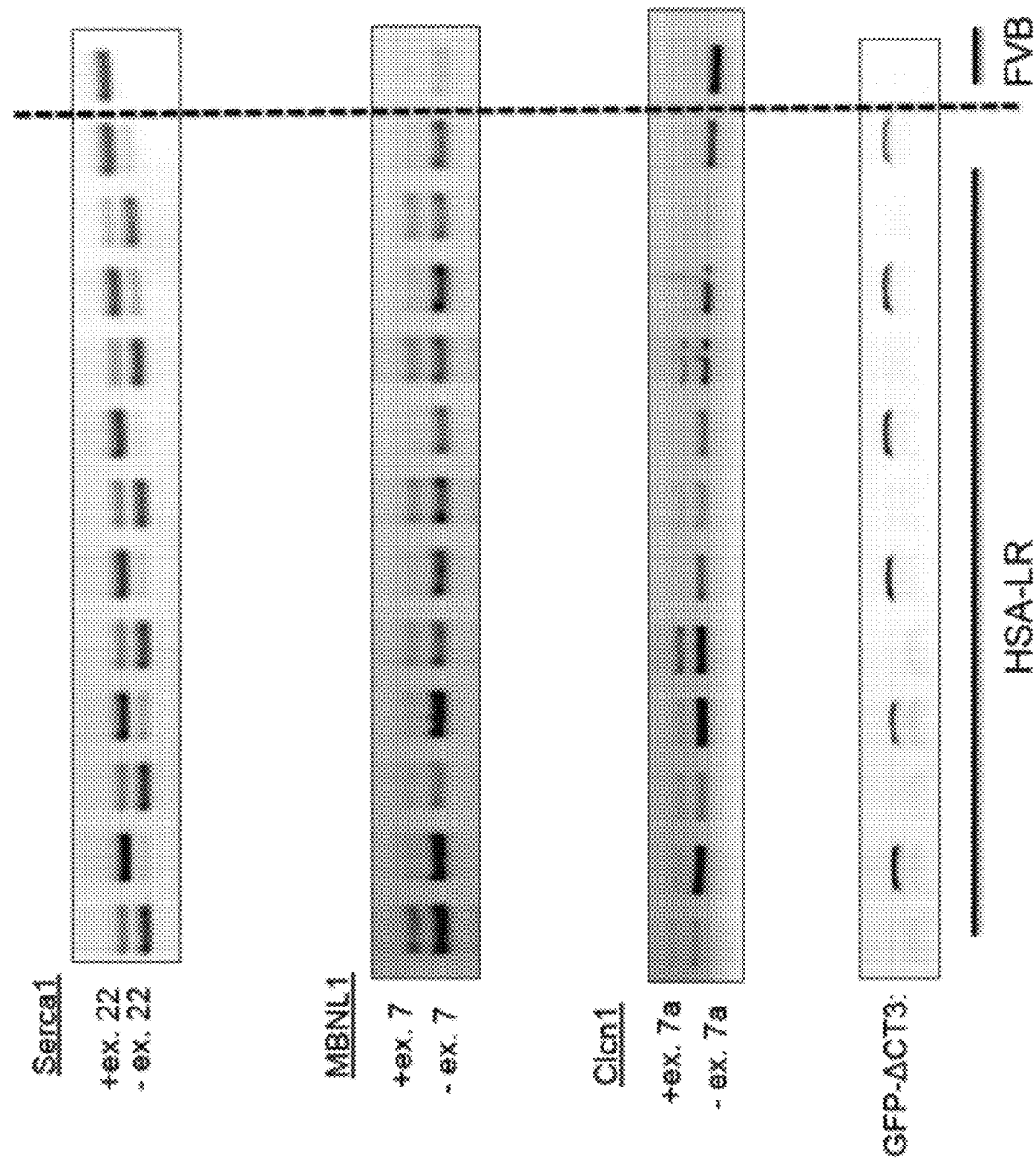
Figure 8:
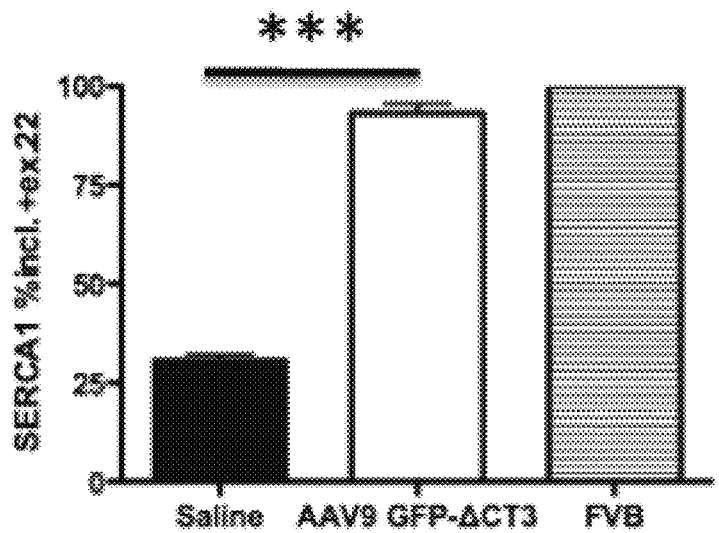
Figure 8:
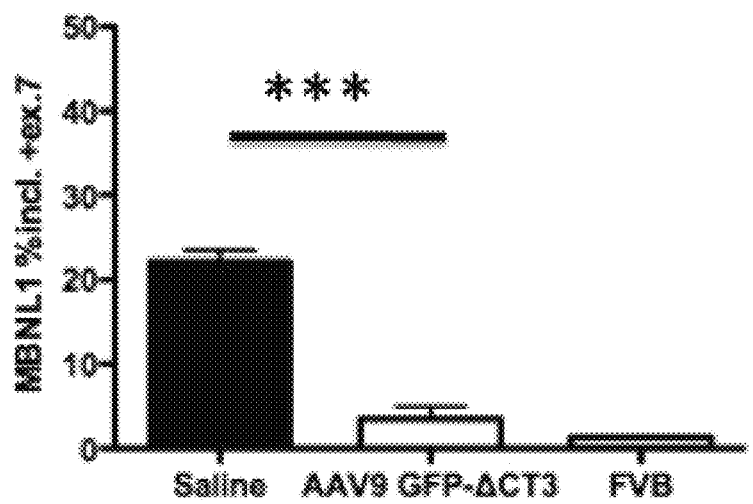
Figure 8:
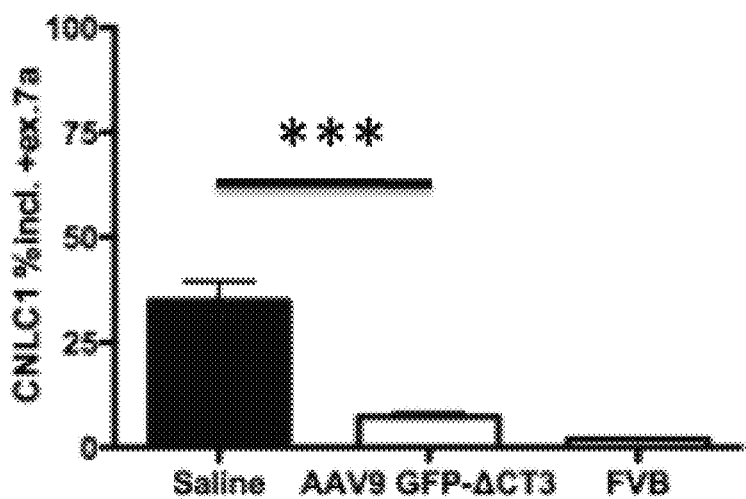

FIG. 8: Intramuscular injection of adeno-associated virus of serotype 9 (AAV9) containing the GFP-ΔCT3 encoding cDNA normalizes splicing misregulations in DM1 mice. Gastrocnemius muscles of HSA-LR mice were injected with AAV9 GFP-ΔCT3 ($1.10^{11}$ vg; n=6) and analyzed after 6 weeks. Contralateral muscles were injected with saline. Splicing profile of Serca1 exon 22, Mbnl1 exon 7 and Clcn1 exon 7a were analyzed by RT-PCR.

Figure 9:
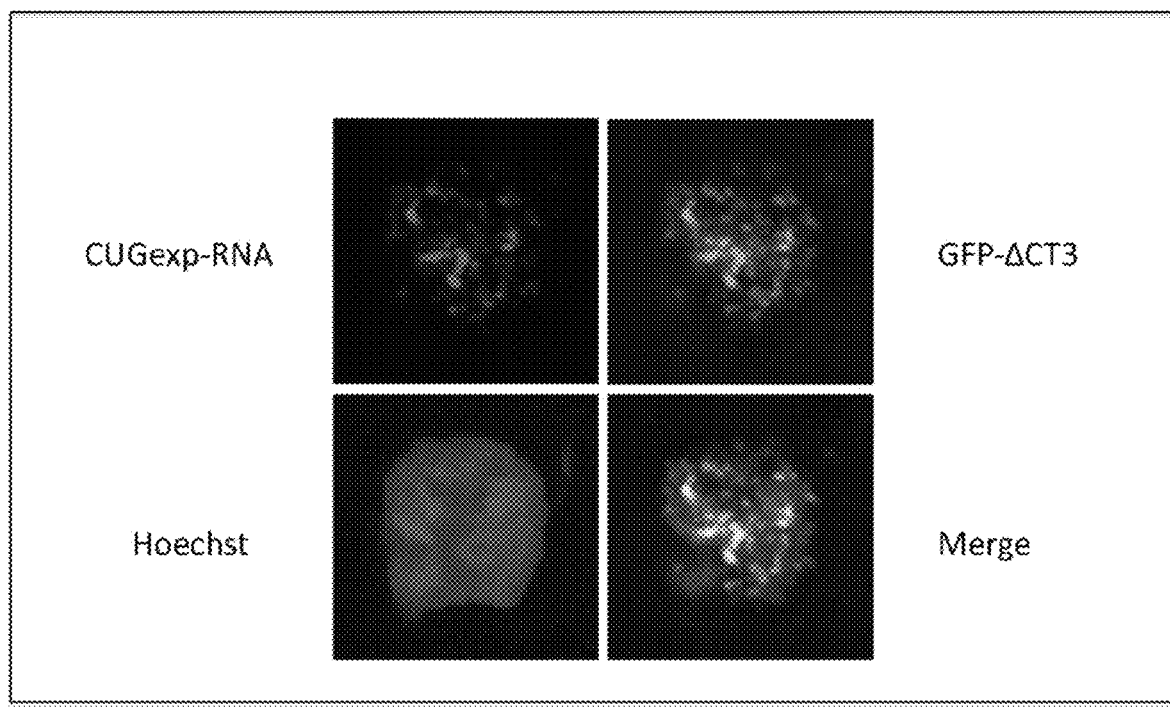

FIG. 9: GFP-ΔCT3 colocalizes with nuclear CUGexp-RNA foci in vivo. FISH-IF were performed to detect CUG-exp-RNA foci and GFP-ΔCT3 on muscle sections of HSA-LR mice injected with AAV9 GFP-ΔCT3.

Figure 10:
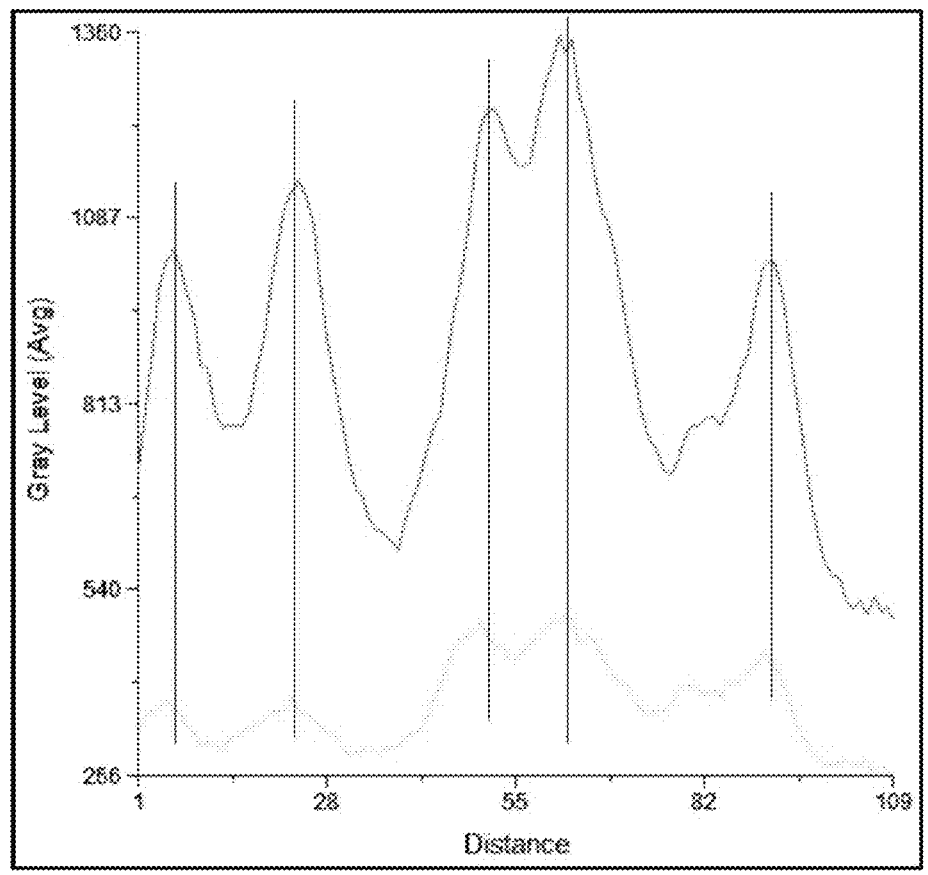
Figure 10:
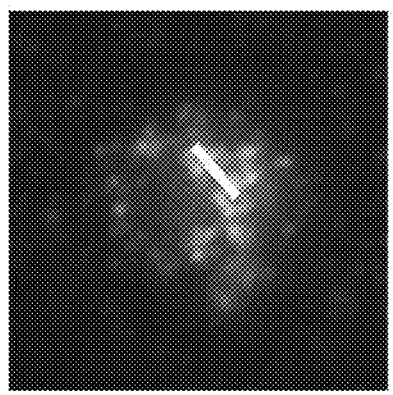
Figure 10:
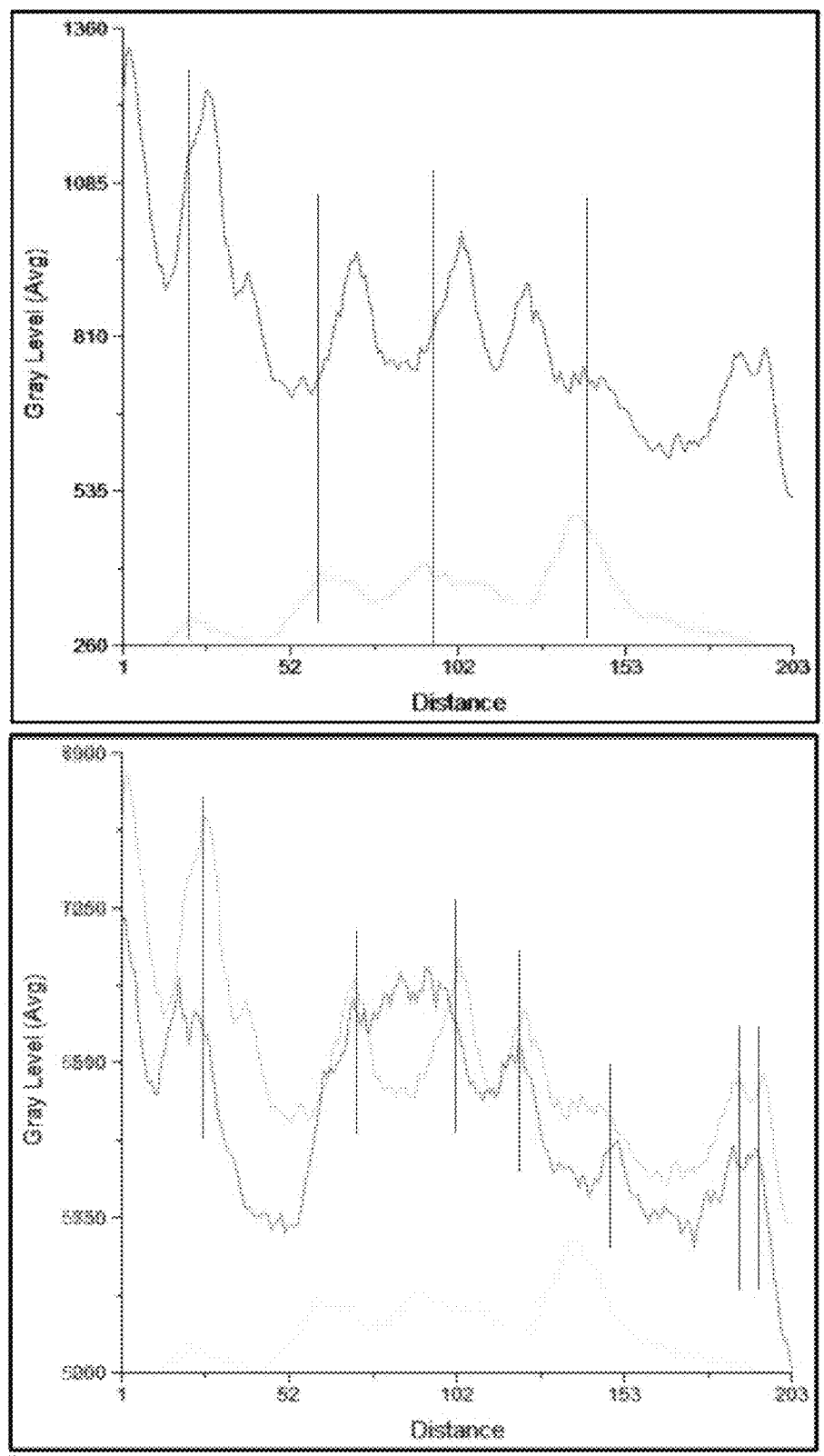

FIG. 10: GFP-ΔCT3 displaces Mbnl1 from nuclear CUG-exp-RNA foci in vivo. FISH-IF were performed to detect CUGexp-RNA foci, endogenous Mbnl1 and GFP-ΔCT3 on muscle sections of HSA-LR mice injected with AAV9 GFP-ΔCT3 or saline. The peak of intensity for each component was measured along an arbitrary lane crossing foci observed within the nucleus.

Figure 11:
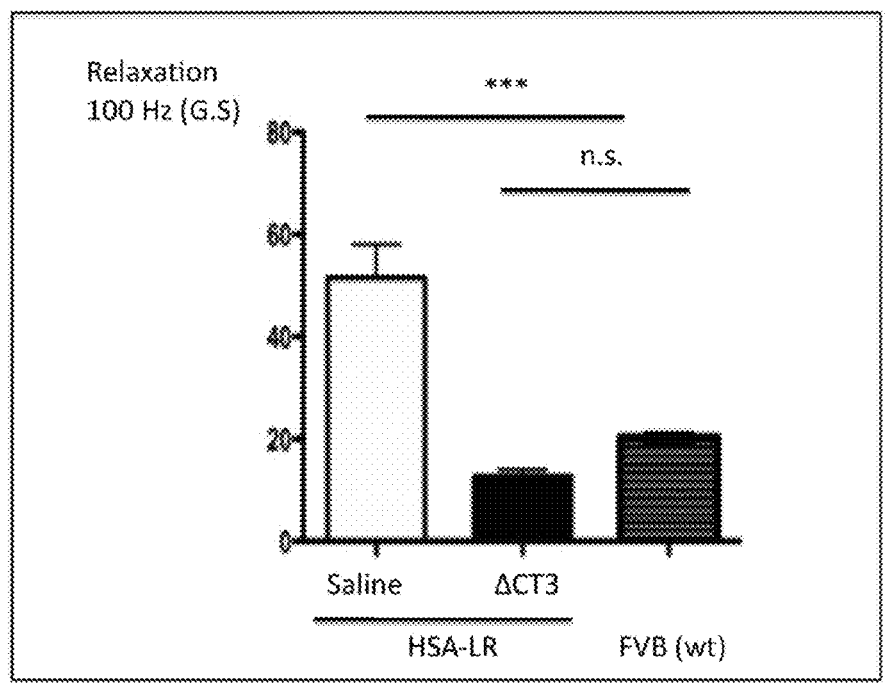

FIG. 11: Intramuscular injection of AAV9 GFP-ΔCT3 abolishes myotonia DM1 mice. Force relaxation of HSA-LR Gastrocnemius muscles injected with AAV9 GFP-ΔCT3 ($1.10^{11}$ vg; n=6) or saline (contralateral muscles) was measured 6 weeks post-injection. Force relaxation was also determined in Gastrocnemius muscles of FVB wt mice.

Figure 12:
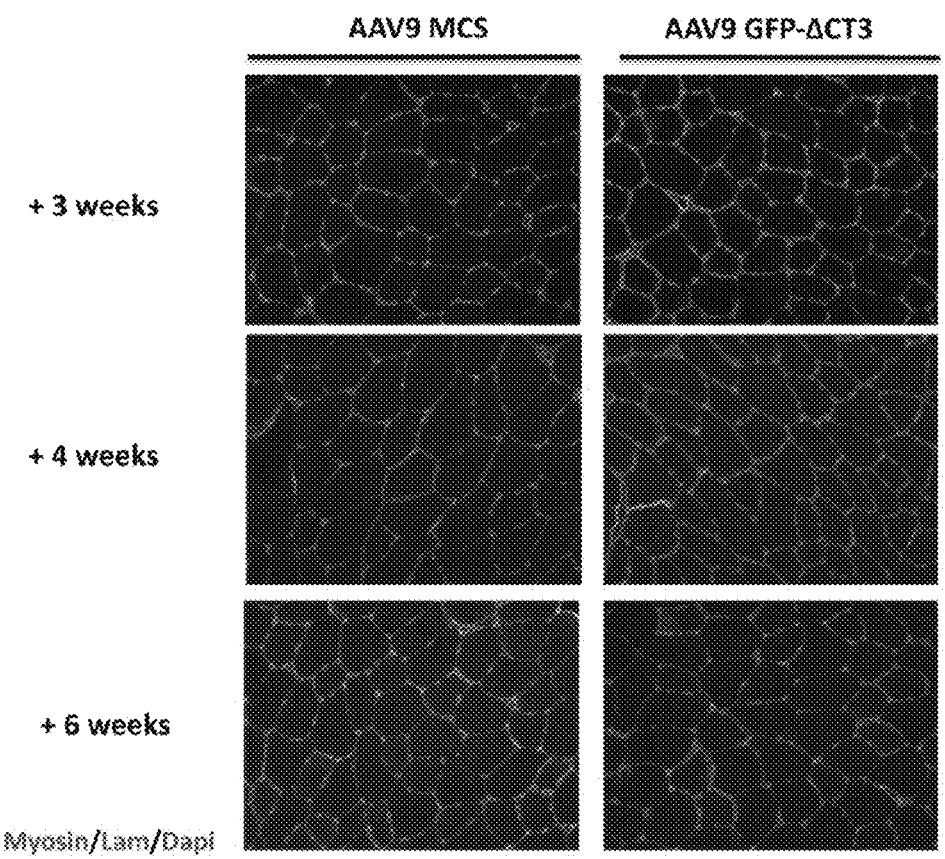

FIG. 12: No signs of muscle degeneration in FVB wt mice expressing AAV9 GFP-ΔCT3. Tibialis anterior muscles of FVB wt mice were injected with AAV9 GFP-ΔCT3 ($1.10^{11}$ vg; n=6) and analyzed by IF after 3, 4 or 6 weeks. Contralateral muscles were injected with empty AAV9 MCS. Embryonic MyHC and laminin antibodies were used to detect regenerating fibers and muscle fibers respectively. Nuclei were stained with Dapi.

Figure 13:
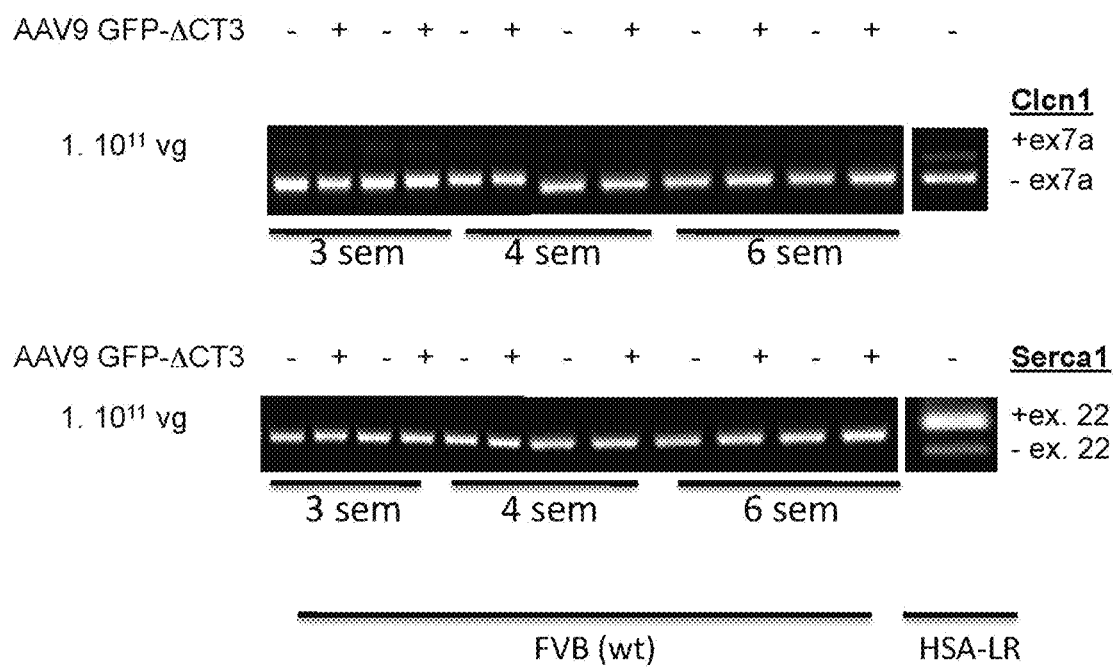

FIG. 13: Expression of AAV9 GFP-ΔCT3 alone did not deregulate alternative splicing in wt mice. Tibialis anterior muscles of FVB wt mice were injected with AAV9 GFP-ΔCT3 ($1.10^{11}$ vg, n=6) and splicing profiles of Clcn1 exon 7a or Serca1 exon 11 were analyzed after 3, 4 or 6 weeks post transduction. Contralateral muscles were injected with empty AAV9 MCS.

Figure 14A:
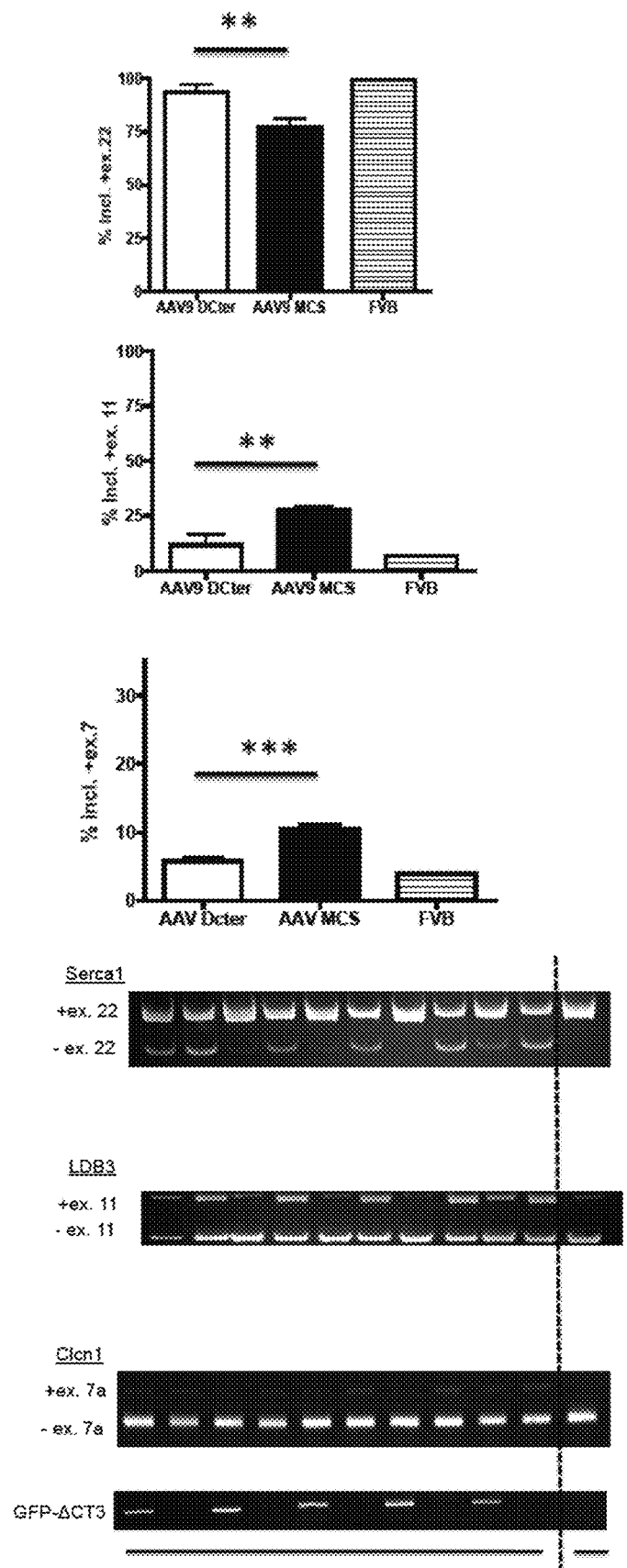

FIG. 14A: Intramuscular injection of AAV9 GFP-ΔCT3 normalises splicing misregulations in DM1 mice. Tibialis anterior muscles of HSA-LR mice were injected with AAV9 GFP-ΔCT3 ($1.10^{11}$ vg; n=6) and analyzed after 6 weeks. Contralateral muscles were injected with AAV9 MCS. Splicing profiles of Clcn1 exon 7a, Serca1 exon 11 and LDB3 exon 11 were determined by RT-PCR.

Figure 14B:
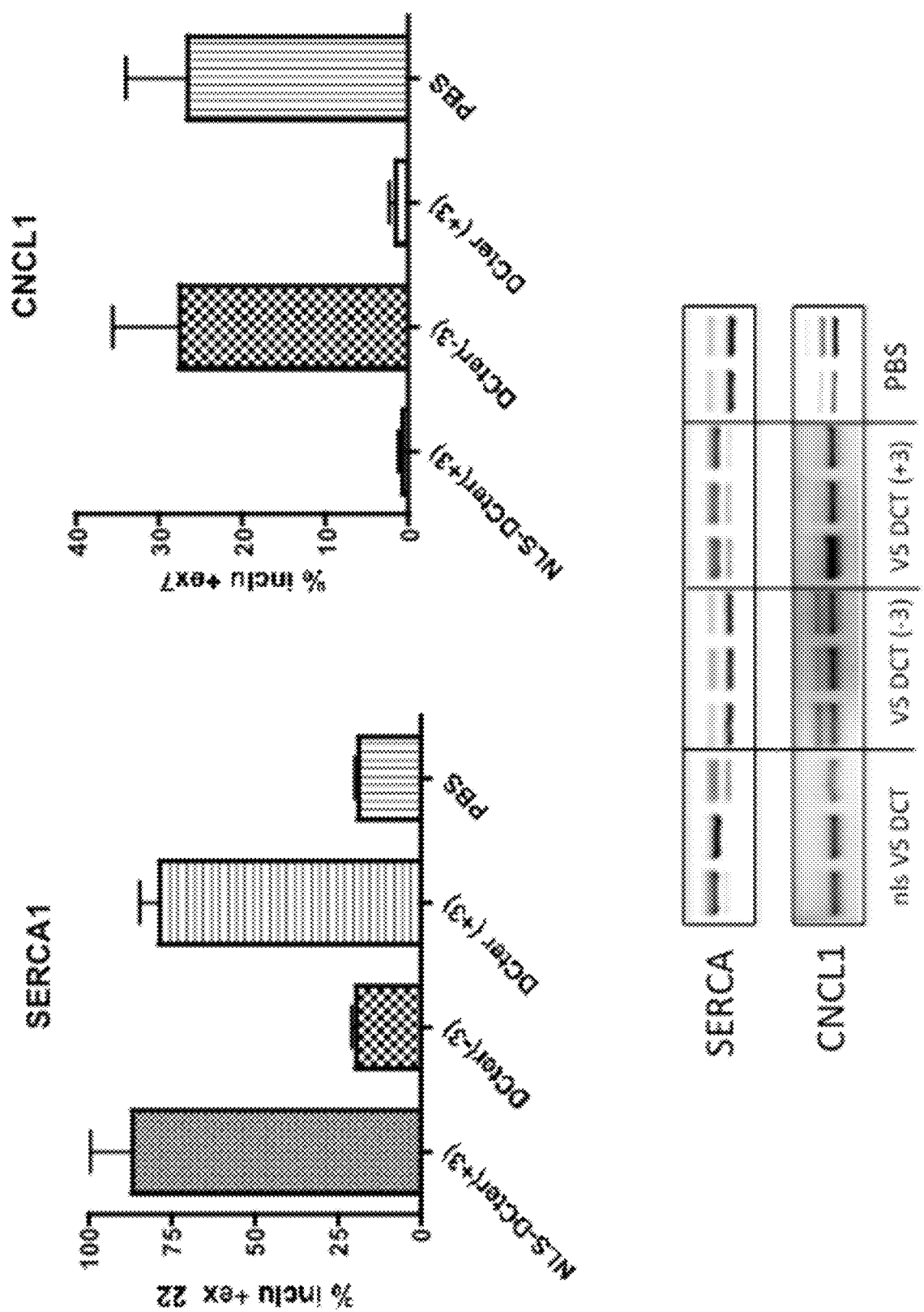

FIG. 14B: Intramuscular injection of AAV9-V5-ΔCT constructs. NLS-V5-ΔCT3 and V5-ΔCT3 constructs normalize splicing misregulations in DM1 mice in contrast to V5-ΔCT (-3) lacking exon 3. Tibialis anterior muscles of HSA-LR mice were injected with AAV9-V5-ΔCT constructs ($5.10^{10}$ vg; n=3) and analyzed after 6 weeks. Contralateral muscles were injected with PBS. Splicing profiles of Clcn1 exon 7a and Serca1 exon 11 were determined by RT-PCR.

Figure 15:
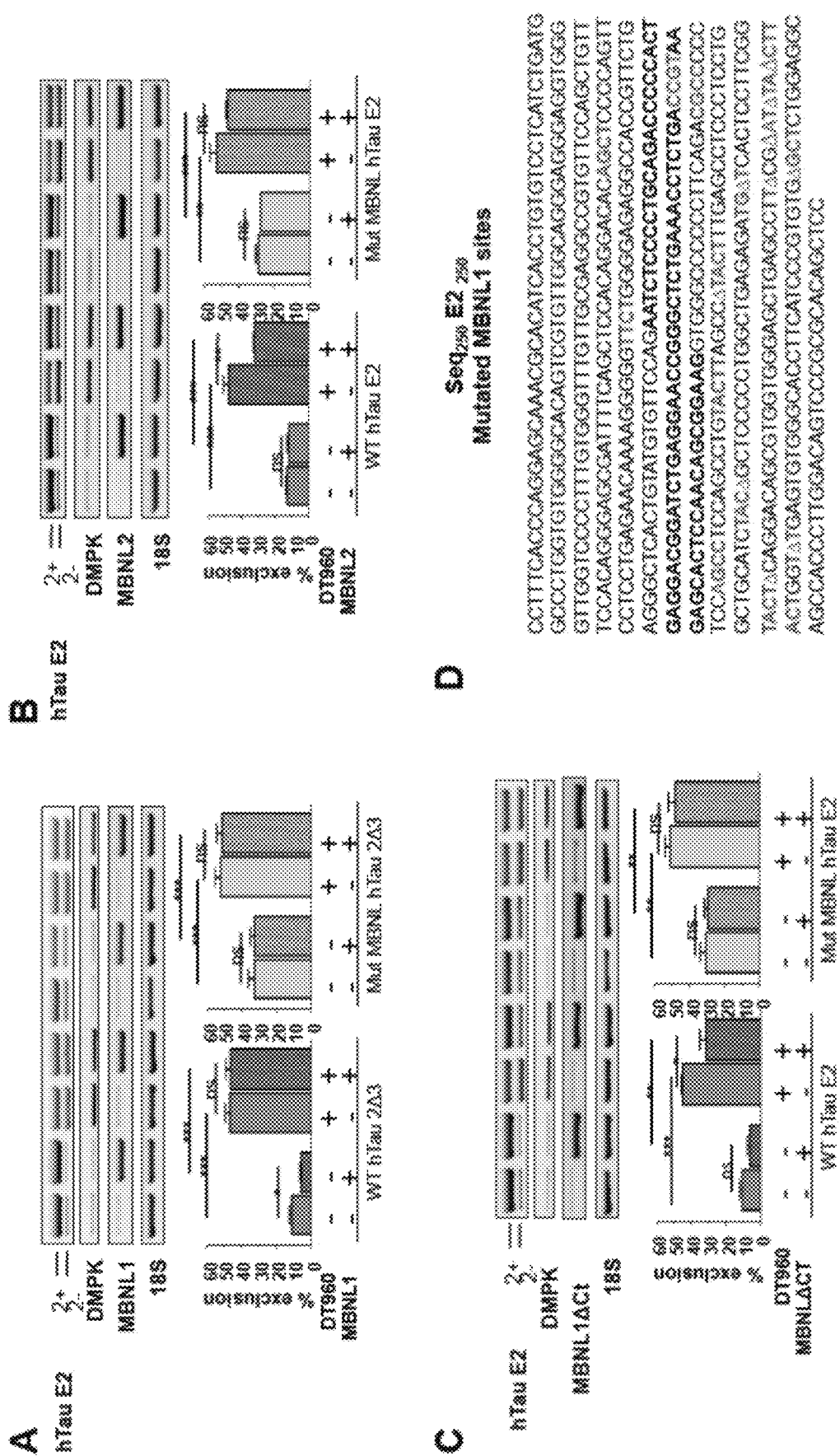

FIG. 15: ΔCT3 restores MBNL-splicing dependent events. MBNL constructs (MBNL1, panel A; MBNL2, panel B; ΔCT3, panel C) were co-expressed with hTau exon2 minigene and 960 CTG repeats in T98G cells, as described in (Carpentier et al., 2014). Inclusion of Tau E2 was analyzed by RT-PCR. The graph indicates the percentage of Tau exon 2 exclusion (averaged±S.E.M. for at least three independent experiments). Significant differences are indicated by asterisks: *, $p<0.05$; , $p<0.01$, *, $p<0.001$. 18S transcripts were used as internal controls to verify the amounts of RNA. The efficiency of DT960 transfection was verified by RT-PCR of the 3'UTR of the human DMPK gene.

Panel D shows the mutant MBNL1 sites that have been mutated (bold grey) in the Mut MBNL construct.

DETAILED DESCRIPTION OF THE INVENTION

The modified MBNL polypeptide of the invention is able to bind the MBNL YGCY RNA-motif, with "Y" representing a pyrimidine (uridine or cytosine). In particular, the modified MBNL polypeptide of the invention is able to bind UGCU-motif, which is the building block of the pathological DM1 expanded CUG repeats. In a particular embodiment, the modified MBNL polypeptide of the invention includes or not the amino acids corresponding to exon 3 of the MBNL1 mRNA (accession number NM_021038). In a further embodiment, the modified MBNL polypeptide of the invention lacks the amino acids of SEQ ID NO:1 (SEQ ID NO:1: TQSAVKSLKRPLEATFDLGIPQAVLPPLP-KRPALEKTNGATAVFNTGIFQYQQALAN MQLQQHTAFLPPGSILCMTPATSVVPMVHGATPAT-VSAATTSATSVPFAATTANQIPII SAEHLTSH-KYVTQM) corresponding to exons 5 to 10 of the MBNL1 mRNA.

As used herein, the term "MBNL" denotes all paralogue members of the muscleblind-like RNA-binding protein family and includes in particular MBNL1, -2 and -3. In a particular embodiment, the modified MBNL polypeptide according to the invention is derived from the human MBNL1 protein sequence. In an embodiment, the modified MBNL polypeptide is a MBNL1 protein having the exon 3 encoded sequence but lacking the amino acid sequences encoded by exons 5 to 10 of the MBNL1 gene. In a specific embodiment, the modified MBNL1-derived polypeptide is referred to as ΔCT3 having the following amino acid sequence:

(SEQ ID NO: 2)
MAVSVTPIRDTKWLTLEVCREFQRGTCSRPDTECKFAHPSKSCQVENGRV

IACFDSLKGRCSRENCKYLHPPPHLKTQLEINGRNNLIQQKNMAMLAQQM

QLANAMMPGAPLQPVPMFSVAPSLATNASAAAFNPYLGPVSPSLVPAEIL

PTAPMLVTGNPGVPVPAAAAAAAQKLMRTDRLEVCREYQRGNCNRGENDC

RFAHPADSTMIDTNDNTVTVCMDYIKGRCSREKCKYFHPPAHLQAKIKAA

QYQVNQAAAAQAAATAAAM.

In an embodiment, the modified MBNL polypeptide is a MBNL1 protein lacking both the exon 3 encoded sequence and the sequences encoded by exons 5 to 10 of the MBNL1 gene. In a specific embodiment, the non-functional MBNL1-derived polypeptide is referred to as ΔCT having the following amino acid sequence:

(SEQ ID NO: 3)
MAVSVTPIRDTKWLTLEVCREFQRGTCSRPDTECKFAHPSKSCQVENGRV

IACFDSLKGRCSRENCKYLHPPPHLKTQLEINGRNNLIQQKNMAMLAQQM

QLANAMMPGAPLQPVVCREYQRGNCNRGENDCRFAHPADSTMIDTNDNTV

TVCMDYIKGRCSREKCKYFHPPAHLQAKIKAAQYQVNQAAAAQAAATAAA

M.

In another embodiment, the modified MBNL polypeptide is a MBNL2 protein encoded by the amino acid sequences of exons 2 to 5 of the MBNL2 protein. In a specific embodiment, the modified MBNL2-derived polypeptide is referred to as MBNL2-ΔCT3 having the following amino acid sequence:

(SEQ ID NO: 4)
MALNVAPVRDTKWLTLEVCRQFQRGTCSRSDEECKFAHPPKSCQVENGRV

IACFDSLKGRCSRENCKYLHPPTHLKTQLEINGRNNLIQQKTAAAMLAQQ

MQFMFPGTPLHPVPTFPVGPAIGTNTAISFAPYLAPVTPGVGLVPTEILP

TTPVIVPGSPPVTVPGSTATQKLLRTDKLEVCREFQRGNCARGETDCRFA

HPADSTMIDTSDNTVTVCMDYIKGRCMREKCKYFHPPAHLQAKIKAAQHQ

ANQAAVAAQAAAAAATVM.

As used herein a "variant" of the modified MBNL polypeptide of the invention is a protein having the same or similar binding properties to the YGCY motif, in particular to CUG repeats, as the wild-type MBNL protein it is derived from (in particular MBNL1, 2 or 3) or as the modified MBNL protein of SEQ ID NO: 2, SEQ ID NO:3 or SEQ ID NO:4 as shown above, and wherein said variant has a reduced splicing activity as compared to the wild-type MBNL protein. In other terms, the modified MBNL polypeptide used in the present invention is a non-functional MBNL polypeptide, that has low or even no splicing activity as compared to the wild-type parent MBNL protein. The use of such a non-functional MBNL polypeptide with regard to its splicing activity has never been reported in the prior art for the treatment of a myotonic dystrophy, since all previous therapeutic attempts were carried out using a functional MBNL protein, i.e. a protein that has all the features of the wild-type protein including its ability to bind to the YGCY motif and its splicing activity. Indeed, previous attempts were aimed at providing to the treated cell overexpression of a MBNL protein that will compensate for the loss of free and functionally available endogenous MBNL proteins which has been sequestered onto pathological repeats. The strategy applied in the present disclosure is unrelated. Instead of providing overexpression of a functional MBNL protein, the inventors propose to introduce into cells in need thereof a modified MBNL protein, i.e. a non-functional variant MBNL protein having reduced or even no splicing activity, to compete, displace, and replace thereon endogenous MBNL protein(s) to avoid the negative consequences of their sequestration. As provided in the experimental part of this disclosure, the results obtained with the present strategy have been extremely satisfying.

In a particular embodiment, the variant according to the invention may have a sequence at least 50%, in particular at least 60%, 70%, 80%, 90% and more particularly at least 95% or even at least 99% identical to the amino acid sequence corresponding to exons 1 to 4 of the wild-type MBNL protein (e.g. of MBNL1, 2 or 3) or to the amino acid sequence shown in SEQ ID NO: 2, 3 or 4.

In a particular embodiment of the invention, the modified MBNL polypeptide of the invention is not a chimeric peptide consisting of a MBNL polypeptide and a targeting moiety.

The present invention implements and modified MBNL polypeptide which has almost no splicing activity, or otherwise said as a reduced activity, as compared to wild-type MBNL protein. By "almost no activity" or "reduced activity", it is herein intended to describe a splicing activity, which is reduced by at least 50%, in particular by at least 60%, 70%, 75%, 80%, 85%, 90% or even at least 95% as compared to the splicing activity of wild-type MBNL protein. Such activity may be determined according to methods well known by those skilled in the art such as the use of minigenes to analyze the alternative splicing of cTNT exon 5, IR exon 11 and Tau exon 2 (Tran et al., 2011).

In a particular embodiment, the modified MBNL protein of the invention may comprise a localization sequence such as a nuclear localization sequence (NLS) or a nuclear export signal (NES). A representative NLS has the sequence represented in SEQ ID NO: 5: PKKKRKV. A representative NES has the sequence represented in SEQ ID NO: 6: LPPLERLTLD. The present disclosure includes any modified MBNL polypeptide as described above, combined with such a localization sequence, in particular with a NLS or NES such as those specifically mentioned above.

The invention further relates to a pharmaceutical composition comprising the modified MBNL polypeptide of the invention or a variant thereof.

Another aspect of the invention is a nucleic acid sequence comprising or consisting of a nucleotide sequence encoding a modified MBNL polypeptide according to the invention. The invention further relates to a genetic construct consisting of or comprising a nucleotide sequence as defined herein, and regulatory sequences (such as a suitable promoter(s), enhancer(s), terminator(s), etc . . . ) allowing the expression (e.g. transcription and translation) of a modified MBNL polypeptide according to the invention in a host cell. The genetic constructs of the invention may be DNA or RNA, and are preferably double-stranded DNA. The genetic constructs of the invention may also be in a form suitable for transformation of the intended host cell or host organism, in a form suitable for integration into the genomic DNA of the intended host cell or in a form suitable for independent replication, maintenance and/or inheritance in the intended host organism. For instance, the genetic constructs of the invention may be in the form of a vector, such as for example a plasmid, cosmid, YAC, a viral encoding vector or transposon. In particular, the vector may be an expression vector, i.e. a vector that can provide for expression in vitro and/or in vivo (e.g. in a suitable host cell, host organism and/or expression system). In a preferred but non-limiting aspect, a genetic construct of the invention comprises i) at least one nucleic acid sequence of the invention; operably linked to ii) one or more regulatory elements, such as a promoter and optionally a suitable terminator; and optionally also iii) one or more further elements of genetic constructs such as 3'- or 5'-UTR sequences, leader sequences, selection markers, expression markers/reporter genes, and/or elements that may facilitate or increase (the efficiency of) transformation or integration or subcellular localization or expression of the modified MBNL polypeptide, such as nuclear localization signal (NLS) or nuclear export signal (NES).

In a particular embodiment, the genetic construct corresponds to the genome of a recombinant viral vector. Suitable viral vectors used in practicing the present invention include retroviruses, lentiviruses, adenoviruses and adeno-associated viruses. In particular, the invention relates to a lentivirus comprising a nucleic acid sequence encoding a modified MBNL polypeptide according to the invention. In another particular embodiment, the invention relates to an AAV vector, in particular an AAV1, AAV2, AAV3, AAV4, AAV5, AAV6, AAV7, AAV8, AAV9, AAV10 or AAV11 vector, in particular an AAV9 vector, comprising a nucleic acid sequence encoding a modified MBNL protein according to the invention. The AVV vector may be a pseudotyped vector, i.e. its genome and its capsid may be derived from different AAV serotypes. For example, the genome may be derived from an, AAV2 genome and its capsid proteins may be of the AAV1, AAV3, AAV4, AAV5, AAV6, AAV7, AAV8, AAV9, AAV10 or AAV11 serotype.

Another aspect relates to a modified MBNL polypeptide according to the invention, for use as a medicament.

The modified MBNL polypeptide of the invention is an useful therapeutic agent, in particular in the treatment of a disease or disorder linked to a sequestration of a MBNL protein, or to a deregulated function of a MBNL member such as MBNL1, or other paralogue members (including MBNL2 and MBNL3). In a preferred embodiment, the modified polypeptide of the invention is used for the treatment of a myotonic dystrophy such as DM1 and DM2, or any disease where a loss of MBNL function (e.g. sequestration, aggregation, mutations . . . ) may be rescued by ectopic delivery of the modified MBNL polypeptide of the invention.

In a further aspect, the invention relates to a modified MBNL polypeptide as described above, for use in a method for the treatment of a myotonic dystrophy.

As used herein, the term "treatment" or "therapy" includes curative and/or preventive treatment. More particularly, curative treatment refers to any of the alleviation, amelioration and/or elimination, reduction and/or stabilization (e.g., failure to progress to more advanced stages) of a symptom, as well as delay in progression of a symptom of a particular disorder. Preventive treatment refers to any of: halting the onset, delaying the onset, reducing the development, reducing the risk of development, reducing the incidence, reducing the severity, as well as increasing the time to onset of symptoms and survival for a given disorder.

It is thus described a method for treating myotonic dystrophies in a subject in need thereof, which method comprises administering said patient with a modified MBNL polypeptide according to the invention, or with a nucleic acid sequence encoding said modified MBNL polypeptide.

Within the context of the invention, "subject" or "patient" means a mammal, particularly a human, whatever its age or sex, suffering of a myotonic dystrophy. The term specifically includes domestic and common laboratory mammals, such as non-human primates, felines, canines, equines, porcines, bovines, goats, sheep, rabbits, rats and mice. Preferably the patient to treat is a human being, including a child or an adolescent.

For the uses and methods according to the invention, the modified MBNL polypeptide, the nucleic acid, the genetic construct, or the viral vector (such as a lentiviral or AAV vector) may be formulated by methods known in the art. In addition, any route of administration may be envisioned. For example, the modified MBNL polypeptide, the nucleic acid, the genetic construct and the viral vector (such as a lentiviral or AAV vector) may be administered by any conventional route of administration including, but not limited to oral, pulmonary, intraperitoneal (ip), intravenous (iv), intramuscular (im), subcutaneous (sc), transdermal, buccal, nasal, sublingual, ocular, rectal and vaginal. In addition, administration directly to the nervous system may include, and are not limited to, intracerebral, intraventricular, intracerebroventricular, intrathecal, intracisternal, intraspinal or perispinal routes of administration by delivery via intracranial or intravertebral needles or catheters with or without pump devices. It will be readily apparent to those skilled in the art that any dose or frequency of administration that provides the therapeutic effect described herein is suitable for use in the present invention. In a particular embodiment, the subject is administered a viral vector encoding a modified MBNL polypeptide according to the invention by the intramuscular route. In a specific variant of this embodiment, the vector is an AAV vector as defined above, in particular an AAV9 vector. In a further specific aspect, the subject receives a single injection of the vector.

Additionally, standard pharmaceutical methods can be employed to control the duration of action. These are well known in the art and include control release preparations and can include appropriate macromolecules, for example polymers, polyesters, polyamino acids, polyvinyl, pyrolidone, ethylenevinylacetate, methyl cellulose, carboxymethyl cellulose or protamine sulfate.

In addition, the pharmaceutical composition may comprise nanoparticles that contain the modified MBNL polypeptide of the present invention.

The below examples illustrate the invention without limiting its scope.

EXAMPLES

Material and Method
Plasmids and Viral Production

The plasmid containing the 3'UTR of DMPK with 960 interrupted CTGs was a minigene vector also under the control of the CMV promoter (kindly gift from T. Cooper, Baylor College of Medecine, Houston Tex., USA). The sequence of MBNL1 full-length variant constructs and truncated ΔCT3 used in this study were previously described (Tran et al. 2011). NES was derived from the REV protein of HIV (Fischer et al. 1995) and fused to the ΔCT3 construct. MBNL1, ΔCT3 and ΔCT3-NES splicing activity was assessed using three minigenes previously described: the RTB300 minigene containing exon 5 of human cTNT (hcTNT); the INSR minigene containing exon 11 of human insulin receptor and the pSVIRB/Tau minigene containing exons 2 and 3. All plasmids DNA were double-strand sequenced at GATC Biotech (France) and purified using the Nucleobond® AX endotoxin free kit (Macherey Nagel, Germany). The cDNA coding for GFP-ΔCT3 or for the GFP protein containing both a Kozak consensus sequence were cloned in the SIN-cPPT-PGK-WHV or pSMD2 transfer vectors. Lentiviral and AAV9 vectors were obtained as previously described (Caillierez et al. 2013; Francois et al.; Fugier et al. 2011) and stored frozen at −80° C. Recombinant GST-MBNL1 and ΔCT3 proteins were produced and UV-cross-linking experiments performed as describe before (Laurent et al. 2012, Tran et al. 2011). The hTau minigene and Mut MBNL construct are described in (Carpentier et al., 2014). Briefly, the hTau E2 minigene consists of exon 1, exon 2 and exon 4 sequences of the human MAPT gene inserted into the pEGFPN1 eucaryote expression vector (Clontech). The exon 2 is preceded and followed by 878 and 2100 nucleotides of the intronic sequences 2 and 3 of the human MAPT gene, respectively (detailed in Carpentier et al., 2014). The Seq250 E2 250 MBNL1 mutated sites in FIG. 15D represents the 250 nucleotides of the intronic sequences surrounding exon 2 for which the MBNL binding sites are mutated (sequences in bold grey). This mutant minigene is no more responsive to MBNL splicing regulatory activity. These minigenes were generated by GeneArt® (Gene Synthesis company) and the sequence of plasmid preparation was verified by double strand sequence by GATC (Biotech, Constance, Germany).

Cell Culture, Transfection and Infection

HeLa cells were grown in monolayer cultures in 6 well plates in Dulbecco's Modified Essential Medium (DMEM) (Invitrogen) supplemented with 10% fetal calf serum (FBS) at 37° C. in a humidified $CO_2$(5%) incubator. Cells grown to ~70% confluence were transiently co-transfected with 1 μg of minigene plasmid DNA, 1 μg of CUG repeats and 3 μg of MBNL plasmid DNA in triplicate, using FuGENE HD transfection reagent (Roche Diagnostics) according to the manufacturer's instructions.

Human muscle cells were isolated from skeletal muscle biopsies as described (Furling et al, 2001), in accordance to French legislation on ethical rules. Wild-type (WT) and DM1 myoblasts were grown in HAM's F10 medium supplemented with 20% FBS and 5 μg/mL gentamycin (Invitrogen), at 5% CO2 and 37° C. 100 ng P24/μl were used to transduce $2 \times 10^5$ human muscle cells. Vector transduction was performed overnight in the presence of 4 μg/ml of polybrene (Sigma). To trigger differentiation, growth medium was removed from subconfluent cultures and replaced by DMEM medium supplemented with 10 μg/mL insulin (Sigma).

In Vivo Gene Transfer and Experiments

HSA-LR mice were obtained from C. Thornton and control FVB mice from Janvier. All mouse procedures were done according to experimental protocols approved by the Ethic Committee on Animal Resources at the Centre d'Exploration Fonctionnelle of Pitie-Salpetriere animal facility and under appropriate biological containment. The gastronemius or tibialis anterior muscles of adult mice were injected respectively with 30 to 100 μl of physiological solution containing or not AAV9 vectors. For each mouse, one muscle was injected with AAV GFP-ΔCT3 and the contralateral muscle was injected with control AAV containing any transgene (MCS) or GFP or vehicle alone (PBS). Six weeks after injections, the isometric contractile properties of the muscles were measured as previously described (Mouisel et al. 2006). Then, the mice were killed, muscles were collected and snap-frozen in liquid nitrogen-cooled isopentane and stored at −80° C.

Fluorescent in Situ Hybridization (FISH) and Immunofluorescence

Fluorescent in situ hybridization (FISH) was done as described using a Cy3-labeled 2-O-methyl RNA $(CAG)_7$ probe. Combined FISH-immunofluorescence (IF) experiment was done as described (Francois et al.) using polyclonal MBNL1 (Everest Biotech.) or GFP (Invitrogen) antibodies followed respectively by secondary Cy5- or Alexa 488-conjugated antibodies. Pictures were captured using a Leica confocal microscope and software (Leica microsytems), and processed with ImageJ software. Immunofluorescence on muscle section was done as described using embryonic MyHC (Novocastra) and Laminin (Novocastra) antibodies.

Protein Extraction and Western Blot Analysis

Western blotting was performed with standard methods as described previously (Tran et al. 2011) using anti-GFP (Santa Cruz) or anti-GAPDH (Tebu-Bio) antibodies.

RNA Extraction and Semi-Quantitative Analysis

Total RNA was isolated using a total RNA extraction kit (Nucleospin® RNA II kit, Macherey Nagel) or TRIzol reagent (Invitrogen) according to the manufacturer's protocol. RNA concentration was determined by measuring the absorbance at 260 nm by using the Nanodrop (Labtech). RT-PCR was performed using 1 μg of total RNA using random hexamers and the M-MLV reverse transcriptase (Invitrogen) according to standard protocols. No DNA amplification was observed in the RT controls. PCR was carried out as previously described. The reaction products were resolved by electrophoresis using a 5% or 8% polyacrylamide gel, and bands were stained with SYBR Gold (Invitrogen). The intensity of SYBR Gold luminescence was measured using a FluoroImager scanner (Claravision). PCR experiments were repeated at least three times.

Statistical Analyses

Statistical analyses were performed using unpaired t-test with two tails P values, with the help of Prism 6 Software (GraphPad Software Inc.).

Results

In a previous study focused on binding-affinity and splicing activity of the different MBNL1 iso forms, we showed that truncated MBNL1 construct lacking the C-terminal domain (ΔCT3, FIG. 1) keeps YGCY binding property with a slightly lower affinity when compared to full length MBNL1 iso forms but has a dramatic reduction of its splicing activity due to the absence of the sequence encoded by exons 5 to 10 (Tran et al. 2011). To evaluate if the non-functional polypeptide ΔCT3 polypeptide is still able to bind to pathogenic CUG repeats, Hela cells were co-transfected with expanded CUG repeats and MBNL1- or GFP-tagged ΔCT3 constructs. As observed in FIG. 2, GFP-ΔCT3 colocalizes with the nuclear foci of CUGexp-RNA as observed for the full length MBNL1. We next examined its effect on DM1 deregulated splicing events by co-expressing GFP-ΔCT3 or MBNL1 constructs with expanded CUG repeats and analyze the Tau exons 2/3 splicing using a splicing reporter minigene in Hela cells (FIG. 3). In the presence of CUG repeats, inclusion of Tau exon 2 is significantly reduced as observed in DM1 patients, and over-expression of various MBNL1 isoforms that have similar splicing activities (Tran et al. 2011) restores partially Tau exon 2 inclusion (FIG. 3A). However, over-expression of the GFP-ΔCT3 construct that has more than 80% reduction of its splicing activity compared to MBNL1 also corrects splicing changes of Tau exons 2/3 minigene to similar extend than MBNL1 (FIG. 3B). This result suggests that the GFP-ΔCT3 may interact with CUG repeats to release functional MBNL1 involved in the regulation Tau exon 2 splicing since it is unlike that the residual splicing activity of GFP-ΔCT3 is sufficient to restore a normal splicing of Tau in the presence of CUG repeats. To confirm this hypothesis, we generated a GFP-ΔCT3 construct fused with a strong nuclear export signal (NES) derived from the REV protein of HIV (Fischer et al. 1995). As expected, the GFP-ΔCT3-NES has a complete cytoplasmic localization when compared to GFP-ΔCT3, which displayed a nucleo-cytoplasmic localization (FIG. 4A). Due to efficient nuclear export and exclusive cytoplasmic localization, GFP-ΔCT3-NES has no more residual splicing activity as shown using hcTNT exon 5 and IR exon 11 minigenes (FIG. 4B). By contrast, co-expression of GFP-ΔCT3-NES with CUG repeats and Tau exons 2/3 splicing reporter minigenes is still able to restore a normal splicing of Tau as observed previously with the full length MBNL1 and GFP-ΔCT3 (FIG. 4C). As shown in FIG. 4A, GFP-ΔCT3-NES colocalizes with the CUGexp-RNA foci but the free remaining unbound GFP-ΔCT3-NES is efficiently exported out of the nucleus, and therefore is no more available for alternative splicing regulation. All together, our results indicate that ΔCT3 reverses the deregulated splicing events in the presence of pathogenic CUG repeats by saturating the CUG binding sites and releasing sufficient quantity of functional MBNL1 from the CUGexp-RNA foci.

To confirm that ΔCT3 can bind to CUG repeats and compete with MBNL1 binding, recombinant MBNL1 protein was cross-linked to in vitro transcribed $^{32}$P RNA containing 95 CUG repeats in the absence or presence of growing concentrations of recombinant ΔCT3 protein, or vise-et-versa (FIG. 5). In both conditions, incremental concentrations of recombinant ΔCT3 or MBNL1 were able to reduced respectively, the amount of recombinant MBNL1 or ΔCT3 indicating that ΔCT3 is able to compete and displace efficiently MBNL1 from CUG repeats.

To assess if ΔCT3 can interact with CUGexp-RNA in DM1 cells and modulate DM1 molecular features as alternative splicing mis regulation, human primary muscle cell cultures of DM1 and non-DM1 patients were transduced or not with lentiviral vectors expressing either GFP-ΔCT3 or GFP. As shown in FIG. 6, GFP-ΔCT3 colocalizes with the nuclear CUGexp-RNA foci in DM1 muscle cells. We next investigated the effects on splicing mis regulation of the DMD, BIN1 and LDB3 transcripts, which are abnormally spliced in differentiated DM1 muscle cells (FIG. 7A) (Francois et al. 2011). Expression of GFP-ΔCT3 significantly normalized the splicing profiles of these transcripts in DM1 cells, whereas it did not affect their splicing in control non-DM1 cells. These results confirm that expression of GFP-ΔCT3 is able to reverse molecular changes induced by toxic CUGexp-RNAs in DM1 muscle cells. Moreover, it also shows that modified GFP-ΔCT3 alone does not modify the splicing of endogenous targets. To further decipher the mechanism of action of the modified GFP-ΔCT3, we silenced MBNL1 using siRNA in GFP-ΔCT3 treated muscle cells. As shown in FIG. 7B, GFP-ΔCT3 required MBNL1 activity to fully restore DMD splicing profile in DM1 muscle cells. It is of note that loss of MBNL1 in control muscle cells alters DMD splicing profile. This result indicates that in DM1 cells, GFP-ΔCT3 has not a direct activity on splicing. Thus, ΔCT3 requires the release of functional MBNL1 from the expanded CUG-RNAs to correct splicing changes in DM1 cells.

The capacity of ΔCT3 to neutralize in vivo the RNA toxicity induced by the expanded CUG repeats was next tested in the DM1 mouse model (HSA-LR) expressing 220 CTG in the 3'UTR of the human skeletal actin gene (Mankodi et al. 2000). These mice accumulate CUGexp-RNA in the nuclei of their skeletal muscle fibers and display missplicing events as well as myotonia. Gastronemius (GAS) muscle of HSA-LR mice was injected intramuscularly with AAV9-GFP-ΔCT3 vectors whereas contralateral GAS was injected with saline solution. After 6 weeks, the contraction properties of these muscles were measured in situ, mice were thereafter sacrificed and the muscles were taken for histological and biochemical analysis. Among the splicing changes in the HSA-LR mice that are similar to those observed in DM1 patients, we examined the splicing mis regulation of Serca1, Mbnl1 and Clc-1. As showed in FIG. 8, injection of AAV9-GFP-ΔCT3 corrected the splicing pattern of these transcripts when compared to HSA-LR contralateral muscles and restores an almost complete normal splicing profile when compared to FVB wt mice. Noticeably, AAV9-GFP-ΔCT3 had no impact on the endogenous splicing of these transcripts in FVB wt mice thus confirming that the ΔCT3 construct had almost no splicing regulatory activity in vivo and (FIG. 13) or in vitro concentration equivalent to the WT MBNL1 protein (Tran et al., 2011). Together, our results suggest that ΔCT3 competes with endogenous MBNL for abnormal binding to expanded CUG repeats leading to the release of sequestered and functional MBNL from the CUGexp-RNA aggregates. To support our data indicating that ΔCT3 releases enough functional Mbnl1 from CUGexp-RNA foci to restore normal alternative splicing profiles in HSA-LR mice, we monitored their nuclear localization on muscle sections (FIG. 9). As expected, ΔCT3 colocalizes with the CUGexp-RNA foci in the myonuclei of AAV9-GFP-ΔCT3 injected HSA-LR mice.

In contrast, Mbnl1:CUGexp-RNA foci colocalization (as indicated by the peak of intensity) that overlaps in control HSA-LR mice was largely reduced in AAV9 GFP-ΔCT3 injected mice (FIG. 10), confirming that ΔCT3 replaces MBNL1 into the foci and displaces enough endogenous MBNL1 to restore functional MBNL-dependant splicing activity in DM1 mice.

At the physiological level, it has been established that myotonia observed in this DM1 mouse model results from abnormal splicing of muscle-specific chloride channel Clc-1 exon 7a (Wheeler et al. 2007). Myotonia that is characterized by muscle hyperexcitability that leads to persistent electrical discharges and delayed force relaxation. Since Clc-1 exon 7a missplicing was almost completely normalized by ΔCT3 expression, its effect on muscle force relaxation was determined after induced-contraction (FIG. 11). Significant increased of force relaxation was measured in HSA-LR muscles when compared to wt FVB mice confirming the myotonia previously established by electromyography in these DM1 mice. Myotonia reveals by abnormal force relaxation was abolished in the GAS muscle of HSA-LR mice injected with AAV9-GFP-ΔCT3 when compared to contralateral muscles whereas no significant changes in muscle strength and muscle histology was detected (data not shown). In addition, Tibialis Anterior (TA) muscles of wt mice were also injected with AAV9-GFP-ΔCT3 or an empty AAV9-MCS and sacrificed after 3, 4 and 6 weeks (FIG. 12). These muscles showed no signs of toxicity or muscle regeneration/degeneration as indicated by the almost absence (less than 1%) of central nuclei, embryonic myosin heavy chain re-expression as well as abnormal size of the muscle fibers. In addition, the splicing profile of genes that are abnormally spliced in DM1 is not perturbed in wt mice by either ΔCT3 expression or AAV9 transduction (FIG. 13). Finally, injection of AAV9-GFP-ΔCT3 in TA muscles of HSA-LR mice also corrects the splicing misregulation of several DM1 genes when compared to contralateral muscles injected with empty AAV9-MCS (FIG. 14A). Moreover, addition of a nuclear localization signal (NLS) to the ΔCT3 construct does not modify ΔCT3 efficacy in HSA-LR mice (FIG. 14B). In contrast, the removal of exon 3 from the ΔCT3 construct prevents its splicing correction activity.

Since MBNL2 is also able to bind to expanded CUG repeats leading to its sequestration, we examined whether splicing changes related to MBNL2 deficiency can be corrected by ΔCT3. As showed in FIG. 15A by co-transfection of hTau E2 minigenes with expanded CUG repeats and MBNL- or GFP-tagged ΔCT3 constructs in T98G cells, overexpression of MBNL1 is not enable to correct the defective splicing of Tau exon 2. In contrast, overexpression of MBNL2 reverse this deregulated splicing event induced by the presence of expanded CUG repeats (FIG. 15B) indicating that the missplicing of hTau E2 minigene induced by the presence of expanded CUG repeats is due to MBNL2 rather than MBNL1 deficiency. ΔCT3 is also able to rescue the defective splicing of Tau exon 2 (FIG. 15C). The rescue effect observed with either MBNL2 or ΔCT3 overexpression was abrogated while using a MBNL mutated minigene (FIGS. 15B and C) with mutated MBNL sites surrounding Tau exon 2 (FIG. 15D) demonstrating that the rescue is not independent of MBNL or not due to an indirect effect. Therefore, ΔCT3 can rescue both MBNL1- and MBNL2-deregulated splicing events by releasing several MBNL paralogues from expanded CUG repeats.

Discussion

In this study we provided evidences that non-functional MBNL (ΔCT3), which is almost devoid of splicing activity is effective to counteract CUGexp-RNA toxicity both in vitro and in vivo. Thus, intramuscular administration of AAV vectors expressing ΔCT3 proteins corrects both alternative splicing misregulation and myotonia in DM1 mice. ΔCT3 expressing only the RNA-binding domain of MBNL1 interacts with the pathogenic CUG repeats and releases sequestered MBNL1 from the nuclear CUGexp-RNA foci. This mechanism restores endogenous functional MBNL1 in DM1 muscle cells and corrects DM1-associated phenotypes in vivo. This finding supports the development of a modified, non-functional MBNLA gene therapy approach as an alternate or complementary therapeutic approach for DM1.

Based on the ability of MBNL to bind to expanded CUG repeats with high affinity, we propose to use MBNL1 RNA-binding domain as a bait to block deleterious interaction of poly-CUG binding proteins to pathogenic repeats. To test this hypothesis, we generated a modified, non-functional MBNL (ΔCT3) that contains only the MBNL1 RNA-binding domain and lacks the C-terminal domains encoded by exons 5 to 10 that are responsible for MBNL1 splicing regulatory activity, MBNL nucleocytoplasmic shuttling and most possibly MBNL oligomerisation (Tran et al. 2011). Our results confirm that ΔCT3 maintains its ability to bind to CUG repeats and colocalizes with CUGexp-RNA in muscle cells, both in vitro and in vivo. As shown by in vitro crosslink assay, ΔCT3 displaces MBNL1 from expanded CUG tracts suggesting that in vivo the binding of ΔCT3 to pathogenic DM1 repeats is able either to block deleterious interaction of MBNL1 as well as other unidentified poly-CUG binding proteins or displace sequestered MBNL1 from the nuclear CUGexp-RNA foci. As a consequence, release of functional MBNL1 will reverse DM1-misregulated events.

Normalization of alternative splicing misregulation by ΔCT3 either in DM1 muscle cells or in skeletal muscle of DM1 mice supports the ability of ΔCT3 to target pathogenic CUG repeats and block access to endogenous MBNL1. However, since in vitro assays have showed that YGCY binding property of ΔCT3 are similar or slightly lower than MBNL1, we wondered whether ΔCT3 is able to directly modulate the MBNL1-regulated events. This seems unlike because splicing activity of ΔCT3 due to the lack of MBNL1 exon 5 to 10 is dramatically reduced when compared to MBNL1 using an in vitro minigene assay, and similar results were obtained with a ΔCT3-NES construct that has no splicing activity due to its strong nuclear export signal. But above all, no splicing changes were detected in wt mice or control human cells expressing ΔCT3. Rather, our results argue in favor of a release of endogenous MBNL1 from the nuclear CUG-exp-RNA foci in muscle cells expressing ΔCT3 that restore functional MBNL1 endogenous activity. While MBNL1 is sequestered and colocalized with CUG-exp-RNA foci in control HSA-LR mice, its localization is less associated with the nuclear foci than ΔCT3 in HSA-LR injected mice. Sequestration of ΔCT3 by CUGexp-RNA displaces endogenous MBNL1 from these abnormal structures resulting in the correction of MBNL1-misregulated events in the DM1 mice.

Our AAV-ΔCT3 strategy is the first gene therapy approach that target CUGexp-RNA to inhibit deleterious of poly-CUG binding proteins and correct their toxic effects in vivo. To date MBNL proteins are almost the only proteins in DM1 human tissue samples that were found sequestered in nuclear foci, and recently, splicing abnormalities present in affected muscles of DM1 patients were mainly associated to functional loss of MBNL1 (Nakamori et al. 2013). Depletion of functional MBNL splicing factors due to their abnormal binding and sequestration by CUGexp-RNA leads to alternative splicing misregulation of specific subset of transcripts and ultimately to pathological changes in DM1 tissues. Thus MBNL1-regulated events were associated to DM1 skeletal muscle defects whereas MBNL2-regulated events were misregulated in DM1 brain. In addition, overexpression of functional MBNL1 (isoforms-40 and -41) using AAV vectors is sufficient to reverse missplicing and myotonia in DM1 mice as confirmed by doubly transgenic HSA-LR:MBNL1-OE mice (Kanadia et al. 2006; Chamberlain and Ranum 2012). This strategy of functional MBNL1 overexpression compensates for the loss of MBNL1 in DM1 mice cells by increasing artificially the level of functional MBNL1. Thus MBNL1 isoforms-40 and -41 were successfully overexpressed in muscles however up to 10 different MBNL1 isoforms with various expression profiles and tissue-specific patterns were described. The function of different iso forms is not completely established yet as showed by the recent report indicating that MBNL1 isoform-43 can interact with Src family kinase (Wang et al. 2012; Botta et al. 2013). In addition, MBNL1 that regulates alternative splicing events is also involved in other RNA processes like mRNA decay and miRNA biogenesis (Rau et al. 2011; Masuda et al. 2012). ΔCT3 that targets CUGexp-RNA will circumvent the question of which isoform of MBNL1 should be overexpressed since sequestered endogenous MBNL1 proteins are released in a tissue-specific manner. Moreover, missplicing of MBNL1 it-self that changes the MBNL1 isoforms ratio in DM1 tissues is corrected in the muscle tissue of DM1 mice expressing ΔCT3. Besides it is not known whether MBNL1 overexpression can restore or compensate for the loss of other MBNL paralogues such as MBNL2. We can presume that ΔCT3 will release other MBNL proteins from CUGexp-RNA and correct MBNL-misspliced events in other tissues than skeletal muscle. Our in vitro results indicate that ΔCT3 is most probably able to compensate for the loss of MBNL2 in a DM1 context (FIG. 15). In fact defective splicing of hTauE2 minigene in the presence of CUGexp-RNA can be restore by either MBNL2 or ΔCT3 but not by MBNL1 overexpression suggesting that ΔCT3 is also able to counterΔCT MBNL2-misregulated events in DM1. Therefore, together our results show that ΔCT3 can counterbalance the effect of CUGexp-RNA deregulated targets which or either regulated by MBNL1, MBNL2 or both. In contrast to a functional MBNL1 overexpression strategy that will compensate for the loss of free and functionally available endogenous MBNL1 due to their sequestration in CUGexp-RNA aggregates, the non-functional ΔCT3 will bind to expanded CUG repeats to release endogenous MBNL1 from CUGexp-RNA aggregates and restore their cellular localization and function.

Among the therapeutic approaches currently under development for DM1, various modified oligonucleotides or small compounds targeting the mutant CUGexp-RNAs have shown promising beneficial effects in vivo (Mulders et al. 2009; Warf et al. 2009; Wheeler et al. 2009; Garcia-Lopez et al. 2011; Sobczak et al. 2012; Wheeler et al. 2012; Leger et al. 2013). Most of these strategies that reverse the muscle phenotype of DM1 mice share a common feature: release of sequestered MBNL paralogues from the CUGexp-RNA foci that leads to its cellular redistribution/relocalization and restores functional MBNL paralogues, resulting ultimately to correction of DM1-associated phenotypes. This mechanism was described for strategies that cause either degradation of the CUGexp-RNAs or steric block of the expanded CUG repeats. Here we propose a novel AAV-ΔCT3 gene therapy for DM1. A single injection of AAV-ΔCT3 was efficient to neutralize RNA toxicity in DM1 mice. In contrast to synthetic oligonucleotides or small compounds that require repeated treatments, AAV vectors have been shown to persist several years in muscles (Rivera et al. 2005) allowing permanent expression of non-functional ΔCT3 that can counterΔCT the continuous expression of toxic CUGexp RNA and trigger a long-lasting effect. Thus, we propose this new gene therapy approach as a valuable alternate or complementary therapeutic approach for DM1.

REFERENCES

Botta, A., A. Malena, et al. (2013). "MBNL142 and MBNL143 gene isoforms, overexpressed in DM1-patient muscle, encode for nuclear proteins interacting with Src family kinases." Cell Death Dis 4: e770.

Brook, J. D., M. E. McCurrach, et al. (1992). "Molecular basis of myotonic dystrophy: expansion of a trinucleotide (CTG) repeat at the 3' end of a transcript encoding a protein kinase family member." Cell 69(2): 385.

Chamberlain, C. M. and L. P. Ranum (2012). "Mouse model of muscleblind-like 1 overexpression: skeletal muscle effects and therapeutic promise." Hum Mol Genet 21(21): 4645-54.

Charizanis, K., K. Y. Lee, et al. "Muscleblind-like 2-mediated alternative splicing in the developing brain and dysregulation in myotonic dystrophy." Neuron 75(3): 437-50.

Charlet, B. N., R. S. Savkur, et al. (2002). "Loss of the muscle-specific chloride channel in type 1 myotonic dystrophy due to misregulated alternative splicing." Mol Cell 10(1): 45-53.

Caillierez R, Begard S, et al. (2013). "Lentiviral delivery of the human wild-type tau protein mediates a slow and progressive neurodegenerative tau pathology in the rat brain". Mol Ther. (7):1358-68.

Carpentier C, Ghanem D, et al. (2014). "Tau exon 2 responsive elements deregulated in myotonic dystrophy type I are proximal to exon 2 and synergistically regulated by MBNL1 and MBNL2". Biochim Biophys Acta. 1842(4): 654-664.

Du, H., M. S. Cline, et al. (2010). "Aberrant alternative splicing and extracellular matrix gene expression in mouse models of myotonic dystrophy." Nat Struct Mol Biol 17(2): 187-93.

Fardaei, M., K. Larkin, et al. (2001). "In vivo co-localisation of MBNL protein with DMPK expanded-repeat transcripts." Nucleic Acids Res 29(13): 2766-71.

Fischer, U., J. Huber, et al. (1995). "The HIV-1 Rev activation domain is a nuclear export signal that accesses an export pathway used by specific cellular RNAs." Cell 82(3): 475-83.

Francois, V., A. F. Klein, et al. (2011). "Selective silencing of mutated mRNAs in DM1 by using modified hU7-snRNAs." Nat Struct Mol Biol 18(1): 85-7.

Fugier, C., A. F. Klein, et al. (2011). "Misregulated alternative splicing of BIN1 is associated with T tubule alterations and muscle weakness in myotonic dystrophy." Nat Med 17(6): 720-5.

Furling. D, L. Coiffier, et al (2001). "Defective satellite cells in congenital myotonic dystrophy" Human Molecular Genetics 10 (19): 2079-87

Garcia-Lopez, A., B. Llamusi, et al. (2011). "In vivo discovery of a peptide that prevents CUG-RNA hairpin formation and reverses RNA toxicity in myotonic dystrophy models." Proc Natl Acad Sci USA 108(29): 11866-71.

Harper, P. S. (2001). Myotonic dystrophy Third Edn., W. B. Saunder, London.

Holt, I., V. Jacquemin, et al. (2009). "Muscleblind-like proteins: similarities and differences in normal and myotonic dystrophy muscle." *Am J Pathol* 174(1): 216-27.

Hunter, A., C. Tsilfidis, et al. (1992). "The correlation of age of onset with CTG trinucleotide repeat amplification in myotonic dystrophy." *J Med Genet* 29(11): 774-9.

Kanadia, R. N., K. A. Johnstone, et al. (2003). "A muscleblind knockout model for myotonic dystrophy." *Science* 302(5652): 1978-80.

Kanadia, R. N., J. Shin, et al. (2006). "Reversal of RNA missplicing and myotonia after muscleblind overexpression in a mouse poly(CUG) model for myotonic dystrophy." *Proc Natl Acad Sci USA* 103(31): 11748-53.

Klein, A. F., E. Gasnier, et al. (2011). "Gain of RNA function in pathological cases: Focus on myotonic dystrophy." *Biochimie* 93(11): 2006-12.

Laurent F X, Sureau A, et al. (2012). "New function for the RNA helicase p68/DDX5 as a modifier of MBNL1 activity on expanded CUG repeats". *Nucleic Acids Res.* 40(7): 3159-71.

Leger, A. J., L. M. Mosquea, et al. (2013). "Systemic delivery of a Peptide-linked morpholino oligonucleotide neutralizes mutant RNA toxicity in a mouse model of myotonic dystrophy." *Nucleic Acid Ther* 23(2): 109-17.

Lin, X., J. W. Miller, et al. (2006). "Failure of MBNL1-dependent post-natal splicing transitions in myotonic dystrophy." *Hum Mol Genet* 15(13): 2087-97.

Mankodi, A., E. Logigian, et al. (2000). "Myotonic dystrophy in transgenic mice expressing an expanded CUG repeat." *Science* 289(5485): 1769-73.

Mankodi, A., M. P. Takahashi, et al. (2002). "Expanded CUG repeats trigger aberrant splicing of ClC-1 chloride channel pre-mRNA and hyperexcitability of skeletal muscle in myotonic dystrophy." *Mol Cell* 10(1): 35-44.

Masuda, A., H. S. Andersen, et al. (2012). "CUGBP1 and MBNL1 preferentially bind to 3' UTRs and facilitate mRNA decay." *Sci Rep* 2: 209.

Miller, J. W., C. R. Urbinati, et al. (2000). "Recruitment of human muscleblind proteins to (CUG)(n) expansions associated with myotonic dystrophy." *EMBO J* 19(17): 4439-48.

Mouisel, E., B. Blondet, et al. (2006). "Outcome of acetylcholinesterase deficiency for neuromuscular functioning." *Neurosci Res* 55(4): 389-96.

Mulders, S. A., W. J. van den Broek, et al. (2009). "Triplet-repeat oligonucleotide-mediated reversal of RNA toxicity in myotonic dystrophy." *Proc Natl Acad Sci USA* 106(33): 13915-20.

Nakamori, M., K. Sobczak, et al. (2013). "Splicing biomarkers of disease severity in myotonic dystrophy." *Ann Neurol.*

Pascual, M., M. Vicente, et al. (2006). "The Muscleblind family of proteins: an emerging class of regulators of developmentally programmed alternative splicing." *Differentiation* 74(2-3): 65-80.

Ranum, L. P. and T. A. Cooper (2006). "RNA-mediated neuromuscular disorders." *Annu Rev Neurosci* 29: 259-77.

Rau, F., F. Freyermuth, et al. (2011). "Misregulation of miR-1 processing is associated with heart defects in myotonic dystrophy." *Nat Struct Mol Biol* 18(7): 840-5.

Rivera, V. M., G. P. Gao, et al. (2005). "Long-term pharmacologically regulated expression of erythropoietin in primates following AAV-mediated gene transfer." *Blood* 105(4): 1424-30.

Savkur, R. S., A. V. Philips, et al. (2001). "Aberrant regulation of insulin receptor alternative splicing is associated with insulin resistance in myotonic dystrophy." *Nat Genet* 29(1): 40-7.

Sobczak, K., T. M. Wheeler, et al. (2012). "RNA interference targeting CUG repeats in a mouse model of myotonic dystrophy." *Mol Ther* 21(2): 380-7.

Taneja, K. L., M. McCurrach, et al. (1995). "Foci of trinucleotide repeat transcripts in nuclei of myotonic dystrophy cells and tissues." *J Cell Biol* 128(6): 995-1002.

Tran, H., N. Gourrier, et al. (2011). "Analysis of exonic regions involved in nuclear localization, splicing activity, and dimerization of Muscleblind-like-1 isoforms." *J Biol Chem* 286(18): 16435-46.

Tsilfidis, C., A. E. MacKenzie, et al. (1992). "Correlation between CTG trinucleotide repeat length and frequency of severe congenital myotonic dystrophy." *Nat Genet* 1(3): 192-5.

Wang, E. T., N. A. Cody, et al. (2012). "Transcriptome-wide regulation of pre-mRNA splicing and mRNA localization by muscleblind proteins." *Cell* 150(4): 710-24.

Warf, M. B., M. Nakamori, et al. (2009). "Pentamidine reverses the splicing defects associated with myotonic dystrophy." *Proc Natl Acad Sci USA* 106(44): 18551-6.

Wheeler, T. M., A. J. Leger, et al. (2012). "Targeting nuclear RNA for in vivo correction of myotonic dystrophy." *Nature* 488(7409): 111-5.

Wheeler, T. M., J. D. Lueck, et al. (2007). "Correction of ClC-1 splicing eliminates chloride channelopathy and myotonia in mouse models of myotonic dystrophy." *J Clin Invest* 117(12): 3952-7.

Wheeler, T. M., K. Sobczak, et al. (2009). "Reversal of RNA dominance by displacement of protein sequestered on triplet repeat RNA." *Science* 325(5938): 336-9.

The invention claimed is:

1. A method of treating myotonic dystrophy disease or disorders caused by abnormal sequestration of the muscleblind-like RNA-binding protein (MBNL) comprising administering, to a subject in need of treatment:
   - a MBNLΔCT3 polypeptide consisting of SEQ ID NO:2, optionally further fused to a nuclear localization sequence (NLS) or a nuclear export sequence (NES); or
   - a nucleic acid encoding said MBNLΔCT3 polypeptide.

2. The method of claim 1, wherein a viral vector genome comprising the nucleic acid encoding said MBNLΔCT3 polypeptide operably linked to control sequences is administered to said subject.

3. The method of claim 2, wherein the viral vector genome is a lentivirus- or AAV-derived vector.

4. The method of claim 3, wherein the AAV vector has a serotype 1, 2, 3, 4, 5, 6, 7, 8, 9, 10 or 11 AAV capsid.

5. The method of claim 4, wherein the AAV vector has a serotype 9 AAV capsid.

6. The method of claim 3, wherein the viral vector is an AAV vector and is administered intramuscularly or directly in the CNS.

7. The method of claim 3, wherein the AAV vector is administered as a single injection.

8. The method of claim 1, wherein said MBNLΔCT3 polypeptide is fused to a NLS or NES sequence and exhibits no splicing activity.

9. The method of claim 8, wherein the NLS sequence is SEQ IS NO: 5.

10. The method of claim 8, wherein the NES sequence is SEQ ID NO: 6.

* * * * *

UNITED STATES PATENT AND TRADEMARK OFFICE
CERTIFICATE OF CORRECTION

| | | |
|---|---|---|
| PATENT NO. | : 10,799,556 B2 | Page 1 of 1 |
| APPLICATION NO. | : 15/303769 | |
| DATED | : October 13, 2020 | |
| INVENTOR(S) | : Denis Furling et al. | |

It is certified that error appears in the above-identified patent and that said Letters Patent is hereby corrected as shown below:

In the Specification

Column 1,
Lines 1-3,
"TREATMENT OF MYOTONIC DYSTROPHY

FIELD OF THE INVENTION" should read
--TREATMENT OF MYOTONIC DYSTROPHY

CROSS-REFERENCE TO RELATED APPLICATION
This application is the U.S. national stage application of International Patent Application
No. PCT/EP2015/058111, filed April 14, 2015.

FIELD OF THE INVENTION--.

Column 14,
Line 11, "MBNLA" should read --MBNLΔ--.

Column 16,
Line 5, "counterΔCT" should read --counteract--.

Signed and Sealed this
Twentieth Day of April, 2021

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 7

<210> SEQ ID NO 1
<211> LENGTH: 130
<212> TYPE: PRT
<213> ORGANISM: homo sapiens

<400> SEQUENCE: 1

Thr Gln Ser Ala Val Lys Ser Leu Lys Arg Pro Leu Glu Ala Thr Phe
1               5                   10                  15

Asp Leu Gly Ile Pro Gln Ala Val Leu Pro Pro Leu Pro Lys Arg Pro
            20                  25                  30

```
Ala Leu Glu Lys Thr Asn Gly Ala Thr Ala Val Phe Asn Thr Gly Ile
            35                  40                  45

Phe Gln Tyr Gln Gln Ala Leu Ala Asn Met Gln Leu Gln Gln His Thr
 50                  55                  60

Ala Phe Leu Pro Pro Gly Ser Ile Leu Cys Met Thr Pro Ala Thr Ser
 65                  70                  75                  80

Val Val Pro Met Val His Gly Ala Thr Pro Ala Thr Val Ser Ala Ala
                85                  90                  95

Thr Thr Ser Ala Thr Ser Val Pro Phe Ala Ala Thr Thr Ala Asn Gln
            100                 105                 110

Ile Pro Ile Ile Ser Ala Glu His Leu Thr Ser His Lys Tyr Val Thr
            115                 120                 125

Gln Met
    130

<210> SEQ ID NO 2
<211> LENGTH: 269
<212> TYPE: PRT
<213> ORGANISM: artificial
<220> FEATURE:
<223> OTHER INFORMATION: delta-CT3 MBNL1-derived polypeptide

<400> SEQUENCE: 2

Met Ala Val Ser Val Thr Pro Ile Arg Asp Thr Lys Trp Leu Thr Leu
 1               5                  10                  15

Glu Val Cys Arg Glu Phe Gln Arg Gly Thr Cys Ser Arg Pro Asp Thr
                20                  25                  30

Glu Cys Lys Phe Ala His Pro Ser Lys Ser Cys Gln Val Glu Asn Gly
            35                  40                  45

Arg Val Ile Ala Cys Phe Asp Ser Leu Lys Gly Arg Cys Ser Arg Glu
 50                  55                  60

Asn Cys Lys Tyr Leu His Pro Pro His Leu Lys Thr Gln Leu Glu
 65                  70                  75                  80

Ile Asn Gly Arg Asn Asn Leu Ile Gln Gln Lys Asn Met Ala Met Leu
                85                  90                  95

Ala Gln Gln Met Gln Leu Ala Asn Ala Met Met Pro Gly Ala Pro Leu
            100                 105                 110

Gln Pro Val Pro Met Phe Ser Val Ala Pro Ser Leu Ala Thr Asn Ala
            115                 120                 125

Ser Ala Ala Ala Phe Asn Pro Tyr Leu Gly Pro Val Ser Pro Ser Leu
 130                 135                 140

Val Pro Ala Glu Ile Leu Pro Thr Ala Pro Met Leu Val Thr Gly Asn
145                 150                 155                 160

Pro Gly Val Pro Val Pro Ala Ala Ala Ala Ala Ala Gln Lys Leu
                165                 170                 175

Met Arg Thr Asp Arg Leu Glu Val Cys Arg Glu Tyr Gln Arg Gly Asn
            180                 185                 190

Cys Asn Arg Gly Glu Asn Asp Cys Arg Phe Ala His Pro Ala Asp Ser
            195                 200                 205

Thr Met Ile Asp Thr Asn Asp Asn Thr Val Thr Val Cys Met Asp Tyr
            210                 215                 220

Ile Lys Gly Arg Cys Ser Arg Glu Lys Cys Lys Tyr Phe His Pro Pro
225                 230                 235                 240

Ala His Leu Gln Ala Lys Ile Lys Ala Ala Gln Tyr Gln Val Asn Gln
                245                 250                 255
```

Ala Ala Ala Ala Gln Ala Ala Thr Ala Ala Ala Met
            260                 265

<210> SEQ ID NO 3
<211> LENGTH: 201
<212> TYPE: PRT
<213> ORGANISM: artificial
<220> FEATURE:
<223> OTHER INFORMATION: delta-CT MBNL1-derived polypeptide

<400> SEQUENCE: 3

Met Ala Val Ser Val Thr Pro Ile Arg Asp Thr Lys Trp Leu Thr Leu
1               5                   10                  15

Glu Val Cys Arg Glu Phe Gln Arg Gly Thr Cys Ser Arg Pro Asp Thr
            20                  25                  30

Glu Cys Lys Phe Ala His Pro Ser Lys Ser Cys Gln Val Glu Asn Gly
        35                  40                  45

Arg Val Ile Ala Cys Phe Asp Ser Leu Lys Gly Arg Cys Ser Arg Glu
    50                  55                  60

Asn Cys Lys Tyr Leu His Pro Pro His Leu Lys Thr Gln Leu Glu
65                  70                  75                  80

Ile Asn Gly Arg Asn Asn Leu Ile Gln Gln Lys Asn Met Ala Met Leu
                85                  90                  95

Ala Gln Gln Met Gln Leu Ala Asn Ala Met Met Pro Gly Ala Pro Leu
            100                 105                 110

Gln Pro Val Val Cys Arg Glu Tyr Gln Arg Gly Asn Cys Asn Arg Gly
        115                 120                 125

Glu Asn Asp Cys Arg Phe Ala His Pro Ala Asp Ser Thr Met Ile Asp
    130                 135                 140

Thr Asn Asp Asn Thr Val Thr Val Cys Met Asp Tyr Ile Lys Gly Arg
145                 150                 155                 160

Cys Ser Arg Glu Lys Cys Lys Tyr Phe His Pro Ala His Leu Gln
                165                 170                 175

Ala Lys Ile Lys Ala Ala Gln Tyr Gln Val Asn Gln Ala Ala Ala Ala
            180                 185                 190

Gln Ala Ala Ala Thr Ala Ala Ala Met
        195                 200

<210> SEQ ID NO 4
<211> LENGTH: 268
<212> TYPE: PRT
<213> ORGANISM: artificial
<220> FEATURE:
<223> OTHER INFORMATION: delta-CT3 MBNL2-derived polypeptide

<400> SEQUENCE: 4

Met Ala Leu Asn Val Ala Pro Val Arg Asp Thr Lys Trp Leu Thr Leu
1               5                   10                  15

Glu Val Cys Arg Gln Phe Gln Arg Gly Thr Cys Ser Arg Ser Asp Glu
            20                  25                  30

Glu Cys Lys Phe Ala His Pro Pro Lys Ser Cys Gln Val Glu Asn Gly
        35                  40                  45

Arg Val Ile Ala Cys Phe Asp Ser Leu Lys Gly Arg Cys Ser Arg Glu
    50                  55                  60

Asn Cys Lys Tyr Leu His Pro Pro Thr His Leu Lys Thr Gln Leu Glu
65                  70                  75                  80

Ile Asn Gly Arg Asn Asn Leu Ile Gln Gln Lys Thr Ala Ala Ala Met
                85                  90                  95

Leu Ala Gln Gln Met Gln Phe Met Phe Pro Gly Thr Pro Leu His Pro
            100                 105                 110

Val Pro Thr Phe Pro Val Gly Pro Ala Ile Gly Thr Asn Thr Ala Ile
            115                 120                 125

Ser Phe Ala Pro Tyr Leu Ala Pro Val Thr Pro Gly Val Gly Leu Val
            130                 135                 140

Pro Thr Glu Ile Leu Pro Thr Thr Pro Val Ile Val Pro Gly Ser Pro
145                 150                 155                 160

Pro Val Thr Val Pro Gly Ser Thr Ala Thr Gln Lys Leu Leu Arg Thr
                165                 170                 175

Asp Lys Leu Glu Val Cys Arg Glu Phe Gln Arg Gly Asn Cys Ala Arg
                180                 185                 190

Gly Glu Thr Asp Cys Arg Phe Ala His Pro Ala Asp Ser Thr Met Ile
                195                 200                 205

Asp Thr Ser Asp Asn Thr Val Thr Val Cys Met Asp Tyr Ile Lys Gly
            210                 215                 220

Arg Cys Met Arg Glu Lys Cys Lys Tyr Phe His Pro Pro Ala His Leu
225                 230                 235                 240

Gln Ala Lys Ile Lys Ala Ala Gln His Gln Ala Asn Gln Ala Ala Val
                245                 250                 255

Ala Ala Gln Ala Ala Ala Ala Ala Thr Val Met
            260                 265

<210> SEQ ID NO 5
<211> LENGTH: 7
<212> TYPE: PRT
<213> ORGANISM: artificial
<220> FEATURE:
<223> OTHER INFORMATION: NLS

<400> SEQUENCE: 5

Pro Lys Lys Lys Arg Lys Val
1               5

<210> SEQ ID NO 6
<211> LENGTH: 10
<212> TYPE: PRT
<213> ORGANISM: artificial
<220> FEATURE:
<223> OTHER INFORMATION: NES

<400> SEQUENCE: 6

Leu Pro Pro Leu Glu Arg Leu Thr Leu Asp
1               5                   10

<210> SEQ ID NO 7
<211> LENGTH: 568
<212> TYPE: DNA
<213> ORGANISM: artificial
<220> FEATURE:
<223> OTHER INFORMATION: mutated MBNL minigene

<400> SEQUENCE: 7
cctttcaccc aggagcaaac gcacatcacc tgtgtcctca tctgatggcc ctggtgtggg      60
gcacagtcgt gttggcaggg agggaggtgg ggttggtccc ctttgtgggt ttgttgcgag     120
gccgtgttcc agctgtttcc acagggagcg attttcagct ccacaggaca cagctcccca     180
gttcctcctg agaacaaaag ggggttctgg ggagaggcca ccgttctgag ggctcactgt     240
atgtgttcca gaatctcccc tgcagacccc cactgaggac ggatctgagg aaccgggctc     300

```
tgaaacctct gaccgtaaga gcactccaac agcggaaggt gggccccct tcagacgccc      360 cctccagcct ccagcctgta cttagcctac tttgagcctc cctcctggct gcatctacgc      420
tccccctggc tgagagatgt cactccttcg gtactcagga cagcgtggtg ggagctgagc      480
cttcgattac ttactggttg agtgtgggca ccttcatccc gtgtggctct ggaggcagcc      540
acccttggac agtcccgcgc acagctcc                                        568
```